United States Patent
Shawver

(10) Patent No.: US 12,362,051 B2
(45) Date of Patent: Jul. 15, 2025

(54) SHIPPING DISRUPTION PREDICTIVE TECHNOLOGY

(71) Applicant: Express Scripts Strategic Development, Inc., St. Louis, MO (US)

(72) Inventor: Briana Shawver, St. Peters, MO (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 739 days.

(21) Appl. No.: 17/514,444

(22) Filed: Oct. 29, 2021

(65) Prior Publication Data

US 2022/0139518 A1     May 5, 2022

Related U.S. Application Data

(60) Provisional application No. 63/107,750, filed on Oct. 30, 2020.

(51) Int. Cl.
| | |
|---|---|
| *G16H 20/10* | (2018.01) |
| *G06N 20/00* | (2019.01) |
| *G06Q 10/0631* | (2023.01) |
| *G06Q 10/0635* | (2023.01) |
| *G06Q 10/083* | (2023.01) |

(52) U.S. Cl.
CPC ............. *G16H 20/10* (2018.01); *G06N 20/00* (2019.01); *G06Q 10/06312* (2013.01); *G06Q 10/0635* (2013.01); *G06Q 10/083* (2013.01)

(58) Field of Classification Search
CPC .. G16H 20/10; G06Q 10/6312; G06Q 10/635; G06Q 30/06
See application file for complete search history.

(56) References Cited

U.S. PATENT DOCUMENTS

| | | |
|---|---|---|
| 6,769,228 B1 | 8/2004 | Mahar |
| 7,430,838 B2 | 10/2008 | Rice |
| 8,706,522 B2 | 4/2014 | Cohan |
| 9,002,754 B2 | 4/2015 | Abhyanker |
| 9,070,101 B2 | 6/2015 | Abhyanker |
| 9,373,065 B1 | 6/2016 | Hoffman |
| 9,373,149 B2 | 6/2016 | Abhyanker |
| 9,697,335 B2 | 7/2017 | Joplin |
| 9,944,419 B2 | 4/2018 | Joplin |
| 9,978,036 B1 | 5/2018 | Eller |
| 10,053,248 B2 | 8/2018 | Joplin |
| 10,325,333 B2 | 6/2019 | Eller |
| 10,621,540 B1 * | 4/2020 | Huddar ................ G06Q 30/018 |

(Continued)

*Primary Examiner* — Rutao Wu
*Assistant Examiner* — Stephen S Swartz
(74) *Attorney, Agent, or Firm* — Harness IP

(57) ABSTRACT

A method for managing medication delivery risk is provided. The method obtains risk data for medication deliveries in an identified geo-spatial location, and generates a predicted risk score based on a machine learning model trained to analyze the risk data. As described herein, the predicted risk score indicates whether a delivery interruption is required for the medication deliveries in the identified geo-spatial location. When the predicted risk score indicates a required delivery interruption, the method (i) removes queue entries for one or more of the medication deliveries from a delivery queue, to implement the required delivery interruption; (ii) generates an interruption notification associated with the required delivery interruption; and (iii) transmits the interruption notification.

20 Claims, 14 Drawing Sheets

(56) References Cited

U.S. PATENT DOCUMENTS

| | | | |
|---|---|---|---|
| 10,942,952 B1 | 3/2021 | Wilczynski | |
| 10,963,832 B2 | 3/2021 | Phillips | |
| 11,466,998 B1* | 10/2022 | Williams | G06Q 10/0635 |
| 2009/0089092 A1* | 4/2009 | Johnson | G06Q 10/06 |
| | | | 705/2 |
| 2013/0024333 A1 | 1/2013 | Jones, Jr. | |
| 2014/0018951 A1 | 1/2014 | Linton | |
| 2014/0019471 A1* | 1/2014 | Linton | G05B 19/418 |
| | | | 707/759 |
| 2014/0149244 A1 | 5/2014 | Abhyanker | |
| 2014/0172727 A1 | 6/2014 | Abhyanker | |
| 2014/0277939 A1 | 9/2014 | Ren | |
| 2014/0330456 A1 | 11/2014 | Lopez Morales | |
| 2016/0027307 A1 | 1/2016 | Abhyanker | |
| 2016/0328781 A1* | 11/2016 | Patel-Zellinger | |
| | | | G06Q 30/0635 |
| 2017/0276507 A1 | 9/2017 | Zacharenko | |
| 2018/0144829 A1 | 5/2018 | Cantor | |
| 2019/0005439 A1* | 1/2019 | Nandury | G06N 3/044 |
| 2019/0114714 A1* | 4/2019 | Jones | H04W 4/026 |
| 2020/0126031 A1* | 4/2020 | Whalen | G06Q 30/018 |
| 2020/0202290 A1* | 6/2020 | Lo | G06Q 20/02 |
| 2020/0394610 A1* | 12/2020 | Chopra | G06Q 10/08355 |
| 2022/0217568 A1* | 7/2022 | Mach | H04W 28/0284 |

* cited by examiner

SHIPPING DISRUPTION PREDICTIVE TECHNOLOGY

CROSS-REFERENCE TO RELATED APPLICATION(S)

This application claims the benefit of U.S. provisional patent application Ser. No. 63/107,750, filed Oct. 30, 2020, which is hereby incorporated by reference.

TECHNICAL FIELD

This document pertains generally, but not by way of limitation, to devices, systems, and methods for shipping disruption prediction, more particularly, using geospatial information systems, and even more particularly, to geospatial information systems for healthcare or medicine delivery, e.g., from a pharmacy.

BACKGROUND

Geofencing technology has many practical uses, including drone management, fleet management, human resource management, network compliance management, marketing, asset management, law enforcement, and home automation. A geofence is a feature in a software program that uses satellite navigation systems such as a global positioning system (GPS) or radio-frequency identification (RFID) technologies to define virtual geographical boundaries.

SUMMARY

Various details for the embodiments of the inventive subject matter are provided in the accompanying drawings and in the detailed description text below.

Techniques described herein provide for shipping disruption prediction. Disruptions can cause issues with shipping of items that are perishable or need to remain within an environmentally controlled range, e.g., temperature, thermal budget, humidity or the like. The techniques can use geospatial information to predict delivery interruptions or delay even before the delivery systems inform the fulfillment of the order at the fulfillment center. A pharmacy can be the fulfillment center. The pharmacy can provide for carrier delivery of drugs, medicines and ancillary items germane to drugs, medicine and their delivery. Accordingly, geospatial information systems can provide data for a healthcare system or a pharmacy to predict disruptions of delivery of care.

An automated fulfillment center, e.g., an automated pharmacy, may ship over 50,000 temperature sensitive items, e.g., medications, to patients annually. A carrier may receive that item from the fulfillment center and deliver the item to the recipient, e.g., patient. During natural disasters, carriers experience delays in affected areas. Previously, the fulfillment center was reactive to carrier notice(s) regarding delays in shipping. As a result, some items were ruined and no longer safe for patient use. The presently described systems and methods use a geospatial information system in conjunction with the fulfillment process to assess where and when packages containing environmentally controlled items to determine if the delivery would be affected by the any adverse delivery conditions, e.g., weather, strike, flight disruptions, roadway disruptions and the like. The system and methods look at the shipping proactively before fulfilling the order or before the order leaves the fulfillment center.

Additionally, the present system and method can predict the needed temperature controlled packaging needed to deliver the package within environmental ranges.

In an example embodiment, recipients (patients or caregivers) can be contacted patients to make alternative delivery arrangements if needed.

The present systems and methods can improve healthcare, e.g., adherence, and patient experience as well as reducing drug waste.

This summary section is provided to introduce aspects of the inventive subject matter in a simplified form, with further explanation of the inventive subject matter following in the text of the detailed description. This summary section is not intended to identify essential or required features of the claimed subject matter, and the particular combination and order of elements listed this summary section is not intended to provide limitation to the elements of the claimed subject matter. Rather, it will be understood that the following section provides summarized examples of some of the embodiments described in the Detailed Description below.

BRIEF SUMMARY OF THE DRAWINGS

In the drawings, which are not necessarily drawn to scale, like numerals may describe similar components in different views. Like numerals having different letter suffixes may represent different instances of similar components. Some embodiments are illustrated by way of example, and not of limitation, in the figures of the accompanying drawings.

DESCRIPTION

Figure 1:
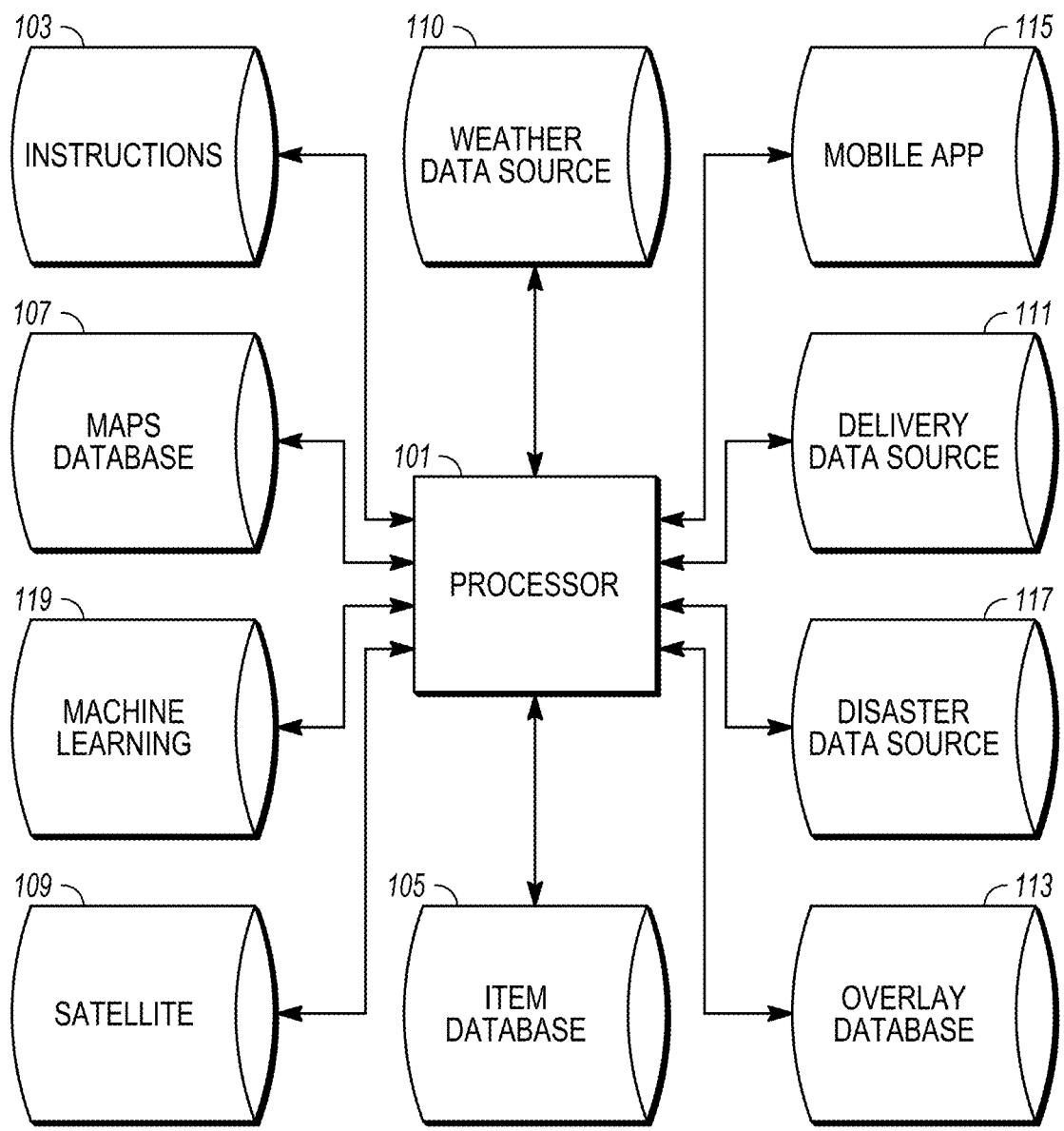
FIG. 1 illustrates a system for determining delivery interruptions, in accordance with the disclosed embodiments.

Reference now will be made in detail to embodiments, one or more example(s) of which are illustrated in the drawings. Each example is provided by way of explanation of the embodiments, not limitation of the present disclosure. It will be apparent to those skilled in the art that various modifications and variations can be made to the embodiments without departing from the scope or spirit of the present disclosure. For instance, features illustrated or described as part of one embodiment can be used with another embodiment to yield a still further embodiment. Thus, it is intended that aspects of the present disclosure cover such modifications and variations.

FIG. 1 illustrates a system 100 that includes a processor 101 that can determine possible interruption of delivery of items. The processor can load instructions from an instruction database 103 to utilize various data sources make the determination. The processor 101 can output flags to delay or not fill an order that may experience delays in delivery and a component of the order may spoil or be unusable after a delayed delivery. The processor 101 can also pull an order from the processing queue if it determines that a delay in delivery by a carrier is likely. The processor 101 can receive inputs from multiple source databases. The processor 101 can be part of a mail order pharmacy.

An item database 105 can store the information related to the ordered item, which can be a component of an order. The item information can indicate if the item is perishable or is subject to environmental controlled delivery.

A maps database 107 can provide map data to the processor. The maps data can include geographical data, such as roads, cities, towns, postal delivery areas, water features, mountains, vegetation and the like.

A satellite data source 109 can provide historical or current satellite data of the area that may receive a delivery.

A weather data source 110 can provide weather data to the processor 101. The weather data can include events that may or are likely to interrupt delivery of an order.

The weather data source 110 is adapted to store weather data for a plurality of defined geographic areas (i.e., geo-spatial locations). Weather data may also include risk data associated with particular weather events. Such weather data may include, without limitation: historical weather events (e.g., tornadoes, hurricanes, floods), previous weather conditions associated with the historical weather events (e.g., wind speeds, quantities of rain or snow and associated flooding, path of storm), previous weather forecasts associated with the historical weather events (e.g., predicted storm path prior to occurrence, predicted wind speeds prior to occurrence, predicted precipitation prior to occurrence). Additionally, some embodiments of the weather data source 110 may be adapted to store current weather data as it occurs in real-time, thus providing the processor 101 access to the current weather data for use in training the machine learning model 119 according to the most up-to-date weather conditions. In this way, the processor 101 is capable of performing updated predictive analysis, in real-time, according to changing weather conditions.

A delivery data source 111 can include data related to actual delivery, e.g., from a carrier that accepts the order package including the item and delivery the package to the end user.

The delivery data source 111 is adapted to store delivery data associated with weather events or disaster events, for a plurality of defined geographic areas (i.e., geo-spatial locations). Such delivery data may include, without limitation: previous actual delivery data and previous delivery predictions associated with weather events or disaster events. The previous actual delivery data may include subsets or "sub-areas" of the defined geographic areas where medication deliveries were actually affected or where conditions affecting medication deliveries were actually affected. As one example, such areas or sub-areas may include transportation routes, and conditions affecting medication deliveries may include (i) any weather or disaster condition affecting viability of the transportation routes, and (ii) available alternative transportation routes in the same area or sub-area. The previous actual delivery data may also include actual delays or interruptions in medication delivery, and whether any delayed or interrupted deliveries were eventually delivered to a recipient by a required medication replenishment deadline. The previous delivery predictions may include any predicted or forecast delivery condition (as described previously with regard to the previous actual delivery data) and whether any of the predicted delivery conditions for a weather event or disaster event actually occurred as a result of the weather event or disaster event An overlay database 113 can provide data related to combining various data sources to provide a composite image that includes data from two or more sources.

A mobile application 115 can provide real-time data from a user. The mobile can show the processed image with overlayed data to a user to confirm delayed deliver or a pause to filling orders associated with a particular geospatial area. The mobile application 115 can also communicate the delay of an order to an end user, e.g., using notification or a secure app on their mobile device in communication with the communication systems of the fulfillment center.

The disaster data source 117 is adapted to store disaster data for a plurality of defined geographic areas (i.e., geo-spatial locations). Disaster data may also include risk data associated with particular disaster events. Disaster events may be natural (e.g., earthquakes, wildfires, sink-holes, accidental building collapse) or man-made (e.g., traffic accidents or congestion, protests, riots, bombings, various forms of civil unrest). Disaster data may include, without limitation: partially or completely physically obstructed roadways inside the defined geographic areas, areas with heavy traffic congestion in one area as a result of roadway obstruction in a second area, visual barriers (e.g., smoke, dust) preventing safe travel in the defined geographic areas, or the like. Additionally, some embodiments of the disaster data source 117 may be adapted to store current disaster data as it occurs in real-time. Like the weather data source 110, the disaster data source 117 thus provides the processor 101 access to the updated disaster data to train the machine learning model 119, such that the processor 101 may perform updated predictive analysis, in real-time, according to changing disaster conditions.

The machine learning model 119, as shown, may refer to one or more of a plurality of machine learning programs, algorithms, data models, or other artificial intelligence (AI) tools implemented for purposes of conducting predictive analysis. The machine learning model 119 is "trained" using historical data, and the trained machine learning model 119 is capable of analyzing current data to make predictions. For purposes of the present disclosure, the machine learning model 119 is trained using weather data and disaster data, such that the machine learning model 119 can be used to analyze current weather or disaster conditions for particular geo-spatial locations and make predictions regarding potential medication delivery interruptions associated with the particular geo-spatial locations. Exemplary embodiments of the machine learning model 119 may be implemented as a ranking model, a propensity weighting model, a spatial weight matrix model, or the like. However, it should be appreciated that other types of machine learning tools may also be used, individually or in combination, such as Logistic Regression (LR), Naïve-Bayes, Random Forest (RF), neural networks (NN), other types of matrix factorization, Support Vector Machines (SVM), or the like.

The various data sources shown in FIG. 1 may be implemented as one or more databases, servers, or other computer data storage media accessible by the processor 101 via the Internet, an intranet, and/or any type of wired or wireless communication connection. Individual ones of the various data sources may be disparately located from the processor 101 and/or the other data sources depicted in FIG. 1. Other embodiments may implement any one of the data sources in the same location as other ones of the data sources and/or the processor 101. For example, a plurality of the data sources may use a common server, data center, or other data storage media or facility. As another example, the processor 101 and one or more of the various data sources may be implemented as a centralized computer system used by one or more pharmacy fulfillment centers.

For purposes of the present disclosure, the processor 101 is configured to obtain risk data associated with events that may hinder or prevent timely medication delivery in defined geographic areas. The processor 101 uses the obtained risk data to train a machine learning model 119 for performing predictive analysis to identify potential medication delivery problems, including current or potential obstructions to physical delivery and/or timely delivery. In certain embodiments, the processor 101 performs active operations to retrieve the risk data, including historical and/or current event data, from the weather data source 110 and the disaster data source 117. For example, the processor 101 may implement a web-crawler, an automated entity (i.e., a "bot"), or other type of data-scraping tool for purposes of obtaining and aggregating data associated with weather events, disaster events, and other events potentially affecting the ability to deliver medications within a required window of time. Alternatively, the processor 101 may implement one or more Application Programming Interfaces (APIs) to retrieve data from the weather data source 110 and/or the disaster data source 117. In some embodiments, however, the processor 101 receives transmitted risk data for use in training the machine learning model 119

Figure 2:
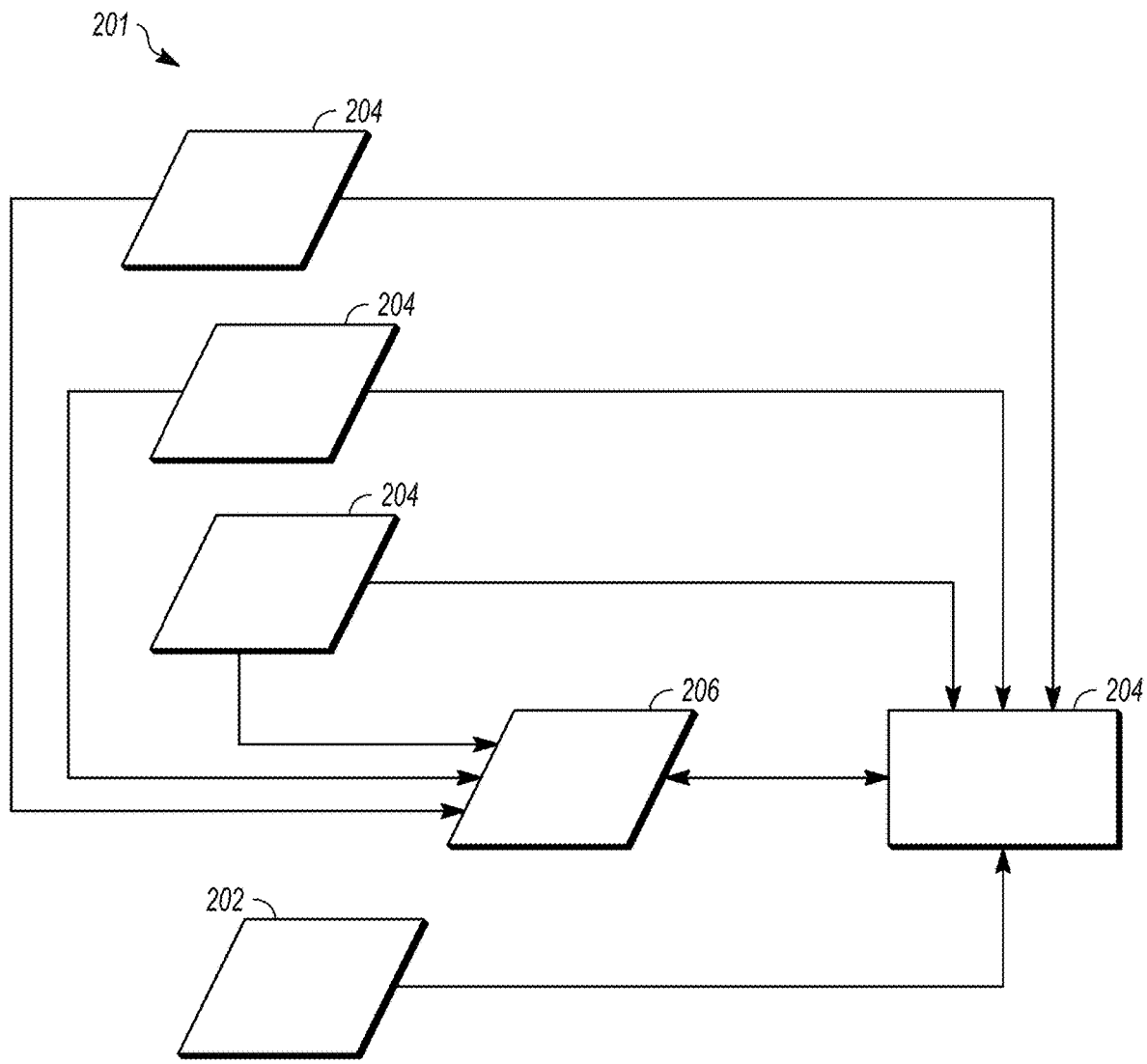
FIG. 2 illustrates an image processing system, in accordance with the disclosed embodiments.

FIG. 2 illustrates an image server 201 that stores a combination of source image data 202 and source overlay data 204. The source image data 202 can be a high-resolution bit-map raster map and or satellite imagery of geographic regions, which can be geographic regions of interest, e.g., where interrupting events are predicted to occur. The overlay image data 204 can be a discrete data file providing image annotation information at defined coordinates relative to the source image data 202. In an example, image annotations may include, for example, street, building and landmark names, as well as representative two dimensional and three dimensional objects, graphical icons, decals, line segments, zip code regions, flood zones, and/or text and or other characters, graphics and or other media.

The network image server 201 can pre-process the source image data 202 and/or source overlay data 204 to generate forms. The forms can represent geographic areas prone to interruptions, e.g., blizzards in the north, floods alone coasts, fires in fire zones and the like.

The source overlay data 204 can be processed 206 into either an open XML format, such as the Geography Markup Language (GML), which is an XML based encoding standard for geographic information developed by the OpenGIS Consortium (OGC; www.opengis.org), or a proprietary binary representation. The XML/GML representation is preferred as permitting easier interchange between different commercial entities, while the binary representation is preferred as more compact and readily transferable to other system components. The source overlay data 204 is pre-processed to contain the annotation data preferably in a resolution independent form associated with a display coordinate specification relative to the source image data 202. The XML, GML or binary overlay data may be compressed prior to storage on in memory.

Figure 3:
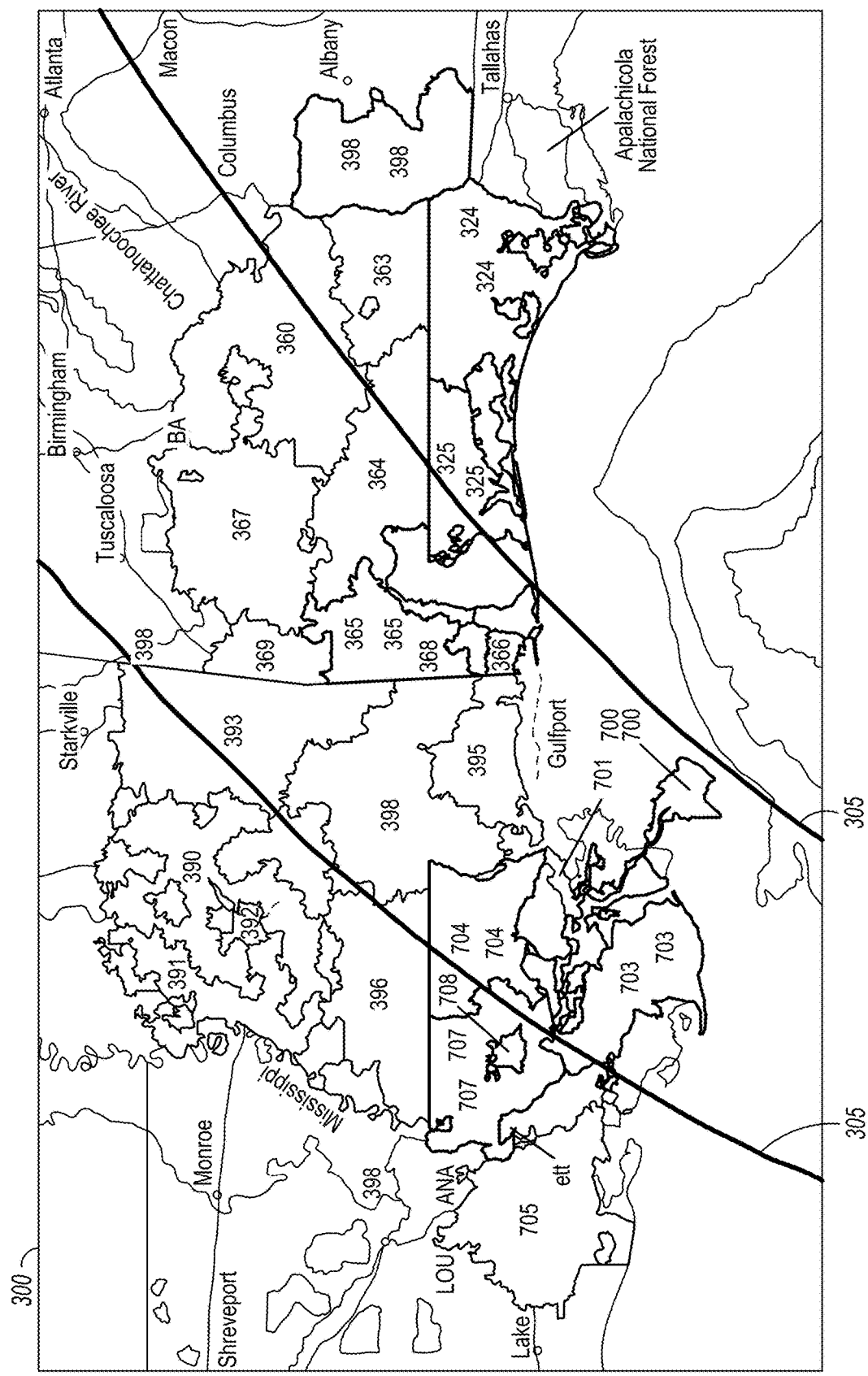
FIG. 3 illustrates a processed image, in accordance with the disclosed embodiments.

FIG. 3 shows an image 300 that can be produced according to the methods and systems described herein. The image 300 can be the source image data 202 with the image overlay data 204 imposed thereon. The image source data can be a large region of interest for delivery of orders that include perishable items. The overlay data 204 can include multiple overlay data. Image 300 starts with a map of the US gulf coast as the source image data 202. The first overlay data 204 can include zip code geographic areas. As shown, the first overlay data 204 is modified to create expanded zip code areas by combining zip code areas that have the same significant digits, here the three significant digits, e.g., 703, 705, 707, 325, etc. The second overlay data 204 can be a predicted path of a weather event, here shown as the lines 305. The third overlay data 204 can be flood zone data. The overlay data can break down the large region of interest into sub-areas. A further data input can be predicted areas (the expanded zip code areas) that will likely affected by the weather event, here shown as the predicted weather path 305. The image 300 shows the areas that should be considered as likely interrupted delivery and the fulfillment center can factor this into when to fill an order with a perishable item or an environmentally controlled item. In an example embodiment, the image 300 can include an overlay of order delivery locations. The order delivery overlay can be a number of prescription orders for a given area. The order delivery overlay can be a number of prescription orders containing time critical components for the given area. The given areas can be the expanded zip codes as shown, zip codes, or delivery areas assigned to a specific delivery vehicle.

Figure 4:
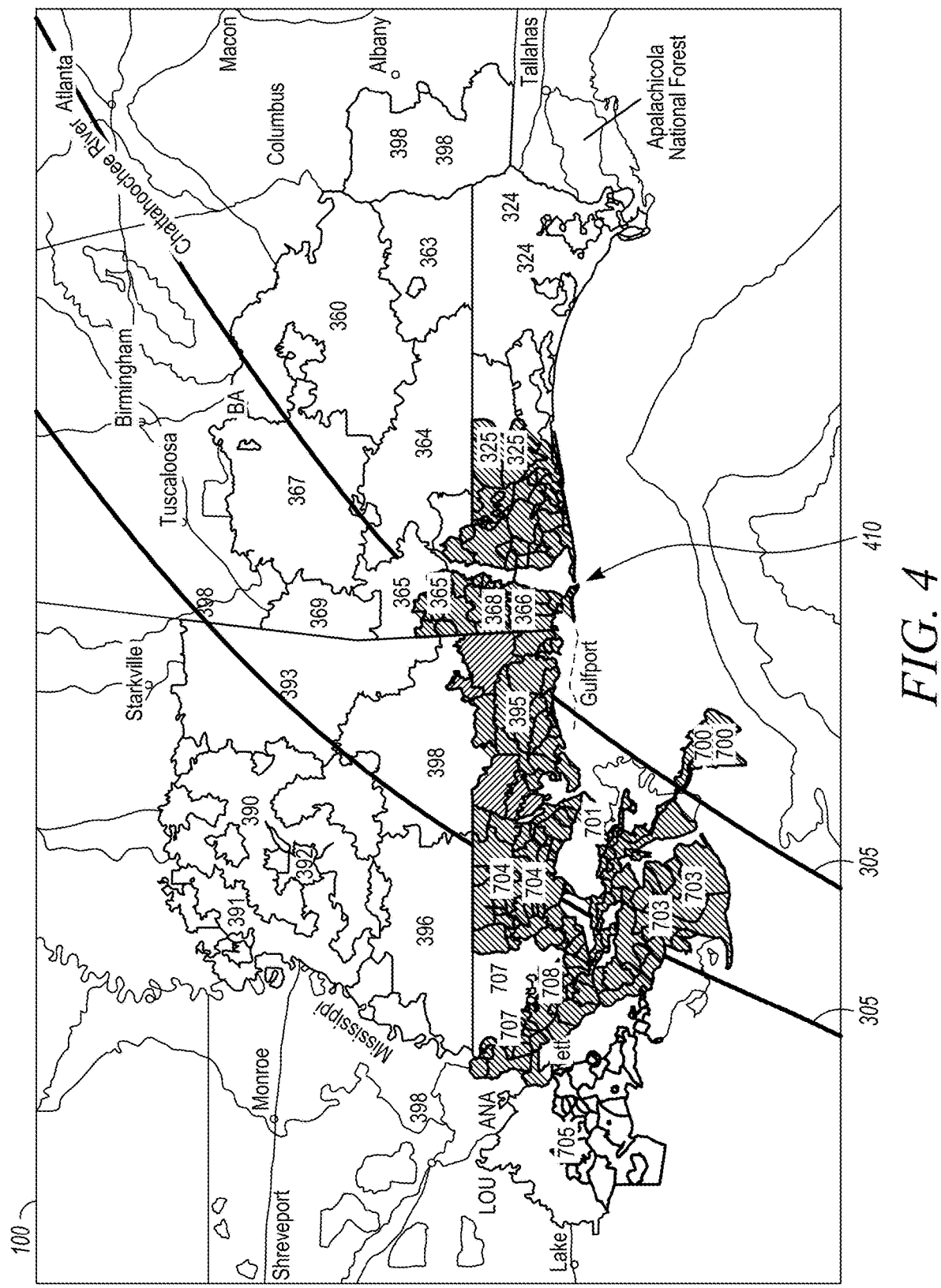
FIG. 4 illustrates a processed image, in accordance with the disclosed embodiments.

FIG. 4 shows an image 400 that can be produced according to the methods and systems described herein. The image 400 is similar to the image 300 but shows geospatial areas 410 that are likely to experience delivery interruptions, e.g., those bounded with solid line and hashed with horizontal lines. The image can be generated by overlay processing of data sets in an electronic system. The image 400 can be created using the methods and systems described herein. The overlay image may present output from a delivery disruption predictive model, which may be used to control the filling of an order, e.g., delay filling until it is likely that the delivery will occur within a set time frame.

An overlay can be an electronic computing operation that superimposes multiple data sets (e.g., weather, predicted weather path, delivery disruption, assigned areas, and the like) together to identify relationships therebetween for the purpose of identifying and addressing potential shipping and delivery issues. The overlay can also represent the routes of delivery services from the fulfillment center, e.g., an automated pharmacy (as described in U.S. Pat. Nos. 9,373,065; 9,697,335; 9,944,419; 9,978,036, and 10,053,248, hereby incorporated by reference) and from the hub of the delivery service to distribution centers and out to recipients. The delivery issues may not be identified individually by a person in real time do to the complexity of the data, the differing sources of the data, the quantity of the data, and the rapidly changing nature of the data. A delivery disruption predictive overlay creates a composite map or visual presentation or a data table for electronic processing by combining the geometry and attributes of the input data sets. When electronically, automatically generating the overlay, the system may use vector data or raster data to generate a visual graphic for presentation on a display.

The weather based data sets can individually represent different weather types, e.g., wind, precipitation, snow, rain, hurricanes, storms, tornadoes, blizzards, fires, and the like. In an example embodiment, the system will interpret the impact of each of these types of weather events based, at least in part, on the type of weather event, the severity of weather event combined with the location of the weather event, a separate data set in an overlay from the weather data sets. For example a snow fall event that has two to three inches of predicted snow may not be disruptive in a northern region, e.g., the Upper Peninsula of Michigan or in Montana, but such snowfall in a southern region, e.g., Texas, may be a severe, disruptive event. Likewise, temperature can be a data set used in the presently described delivery disruption predictive model, freezing temperature are routine in the winter months in the northern regions but southern regions may be predicted to experience transportation delays.

Other data sets that can be fed into the presently described delivery disruption predictive model can include other events that impact transportation systems, including, but not limited to, worker strikes, airplane groundings, civil unrest, roadway outages, fuel disruptions and the like. The presently described delivery disruption predictive model can use the overlay technology to add additional data sets that represent possible delivery delay disruptions to provide a prediction of delivery delays.

Figure 5:
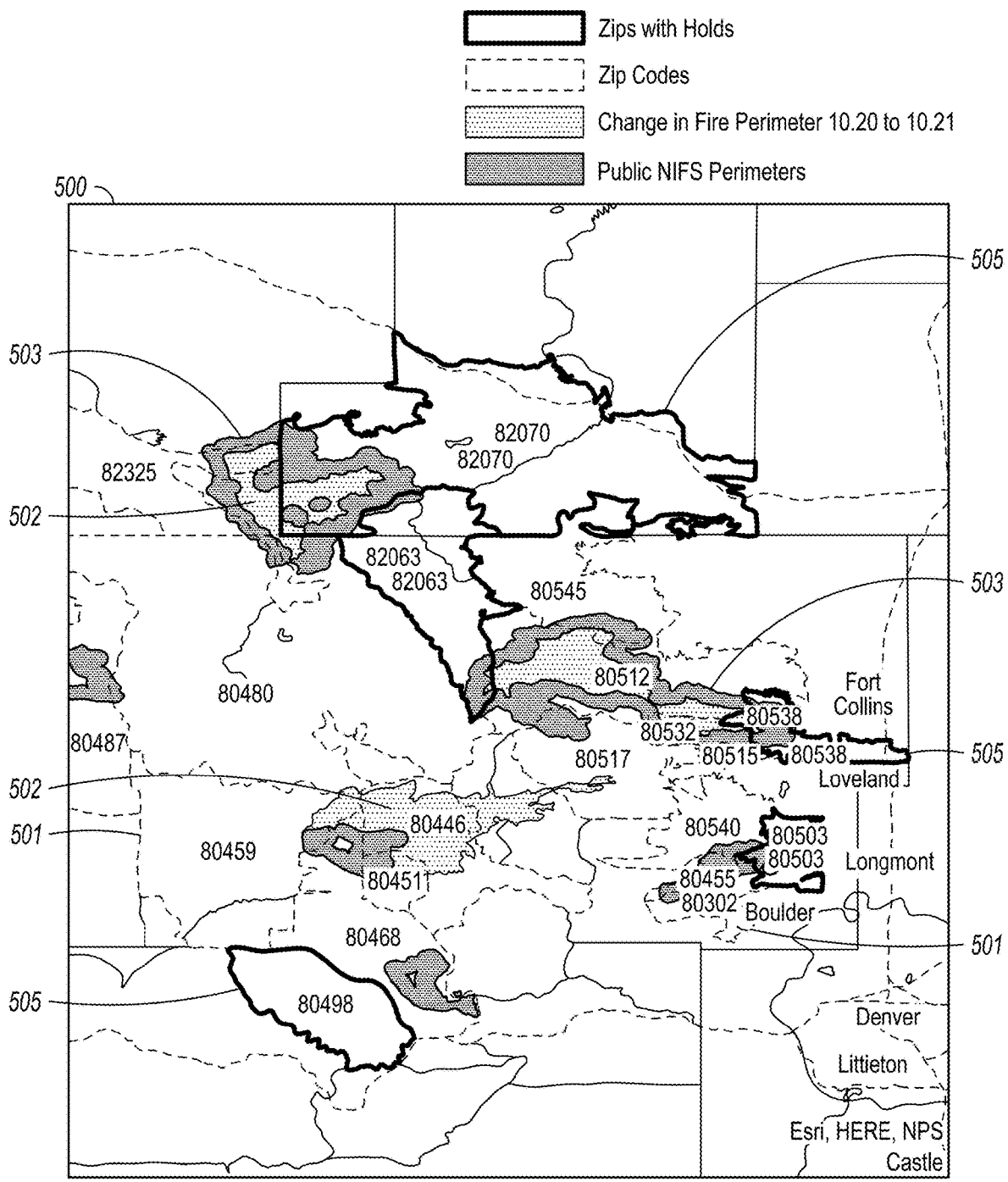
FIG. 5 illustrates a processed image, in accordance with the disclosed embodiments.

FIG. 5 shows an image 500 that can be produced according to the methods and systems described herein. The image 500 shows the area with postal code boundaries 501. Geospatial areas 502 indicate have an adverse event, e.g., a fire. The fire data can be from the national incident feature service (NIFS) hosted by Fire Enterprise Geospatial Portal (EGP). The fire data can be loaded from a database at a governmental agency, e.g., National Interagency Fire Center. The areas 503 can show the change in the perimeter of the adverse event over a period of time. The areas 505 can show areas that will likely have delivery interruptions based on the adverse events. Here, the areas 505 may or may not have an actual or active event in their area, but events in adjacent areas will effect delivery. The areas 505 can include the zip codes 82070, 82063, 80838, 80503, 80498. The areas 505 can also be filtered to those areas that include a scheduled deliver or an upcoming order delivery.

Figure 6:
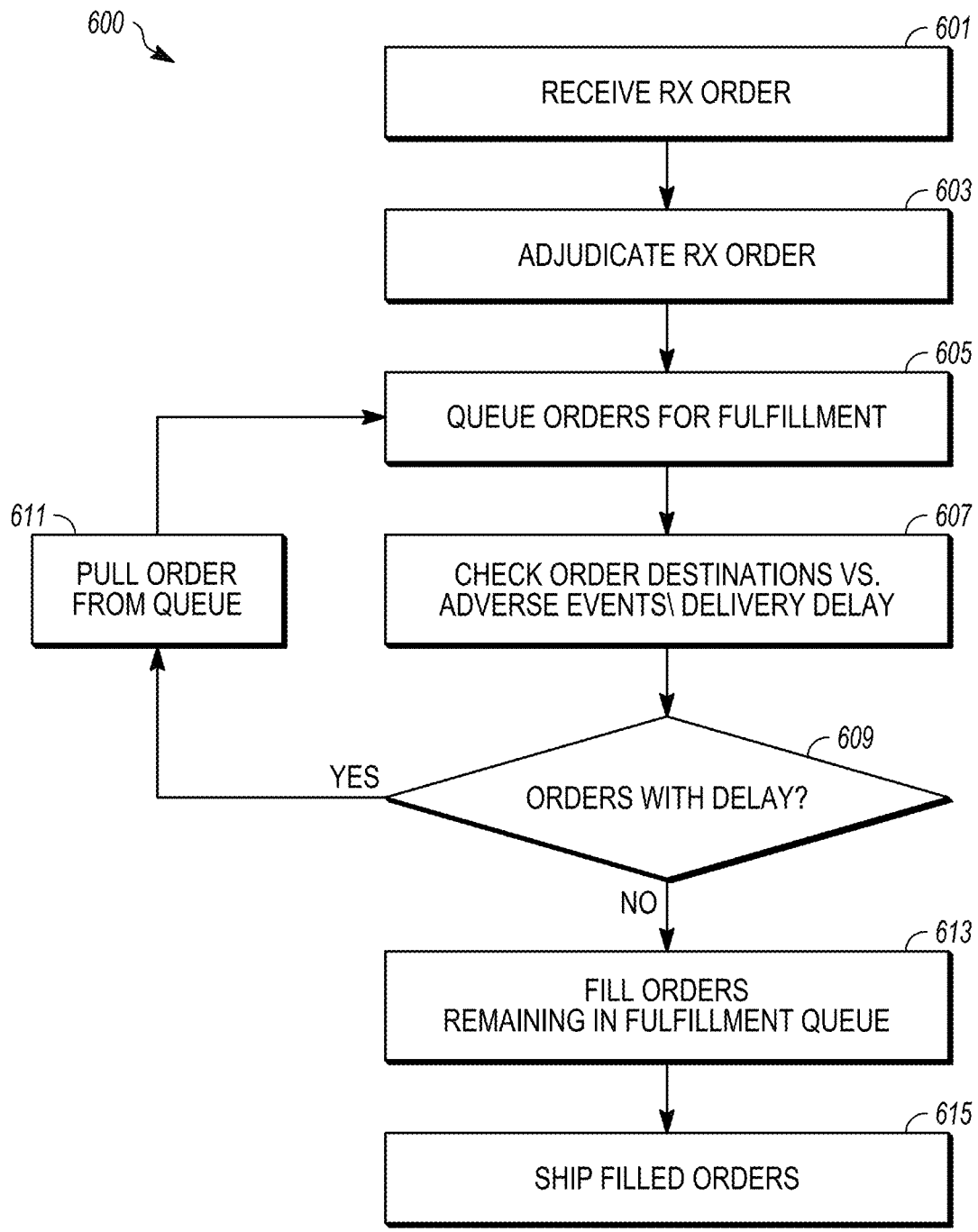
FIG. 6 is a flow chart that illustrates an embodiment of a process for filling prescription orders while considering delivery delays due to adverse events, in accordance with the disclosed embodiments.

FIG. 6 shows a flow chart 600 of a process for filling prescription orders while considering delivery delays due to adverse events.

At 601, a prescription order is received.

At 603, the prescription order is adjudicated.

At 605, adjudicated prescription orders are queued for fulfilment. The fulfillment can include automated mail order pharmacy fulfillment.

At 607, the order destinations are checked versus adverse events that can delay delivery, e.g., the process 700 (FIG. 7) described in greater below.

At 609, it is checked whether an individual order in the order queue includes a delay. If yes there is a delay, then the order is pulled from the fulfillment queue at 611. This pulled order is inserted into a subsequent queue for later fulfillment.

At 613, the orders in the queue that are not delayed, are fulfilled in the pharmacy.

At 615, the filled orders are shipped.

Figure 7:
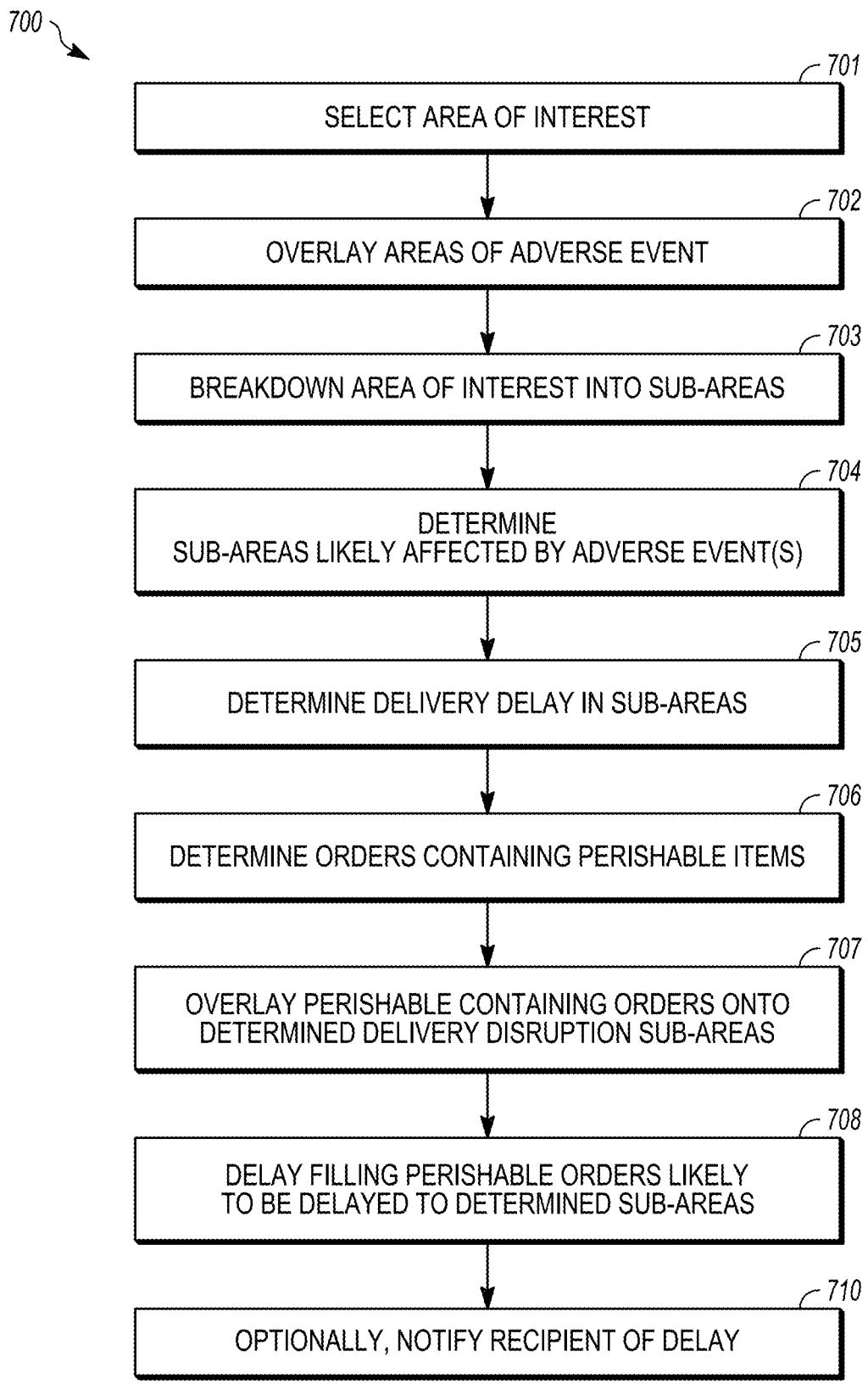
FIG. 7 is a flow chart that illustrates an embodiment of a process for determining whether to delay fulfilling and delivery of an order based on events affecting the delivery area, in accordance with the disclosed embodiments.

FIG. 7 shows a flow chart 700 of a process for determining whether to delay fulfilling and delivery of an order based on events affecting the delivery area.

At 701, the geographical area of interest is selected. The area of interest can be a state, a partial state or multiple states in example embodiments. In an example, the area of interest includes multiple delivery areas and services.

At 702, adverse events are overlaid on the area of interest. The adverse events can be natural disasters or other adverse weather events that delay the delivery of the order to the recipient location. In some cases, the adverse event is in the supply system of the carrier who picks up the order from the fulfillment center and delivers the order to the recipient location.

At 703, the area of interest is broken down into sub-areas. The subareas can be broken down by postal code, e.g., a full five digit zip code in the USA, a +4 zip code in the USA or a three digital postal code. The sub-areas can also be broken down by other criteria.

At 704, the process 700 determines the sub-areas likely to be affected by the adverse event(s).

At 705, it is determined if there is delay in the sub-areas.

At 706, the orders that are to be delivered to the delayed sub-areas are determined. These orders have not yet been filled in an example embodiment. In an example, the orders have not yet left the fulfillment center and remain in an environmentally controlled state at fulfillment center, e.g., in a cooler in a pharmacy.

At 707, the orders with perishable items over overlaid on the sub-areas affected by delivery delay.

At 708, the orders with perishable items are delayed at the fulfillment center for a determined time period for the determined sub-areas. The orders are pulled from the normal processing queue and stored in a priority database. When the time period ends the orders are reprocessed according to the present method to determine if the order should be processed for delivery at the subsequent time, e.g., has the adverse event passed.

Each of the preceding steps in process 700 can produce an updated image output on a display device to visualize the affected areas.

At 710, the process can optionally, contact the recipient of order that there is a delay in the shipment of the order. The notification can be an alert sent through a mobile app loaded on the recipient's electronic device, which is connected with the healthcare services for the user.

Figure 8:
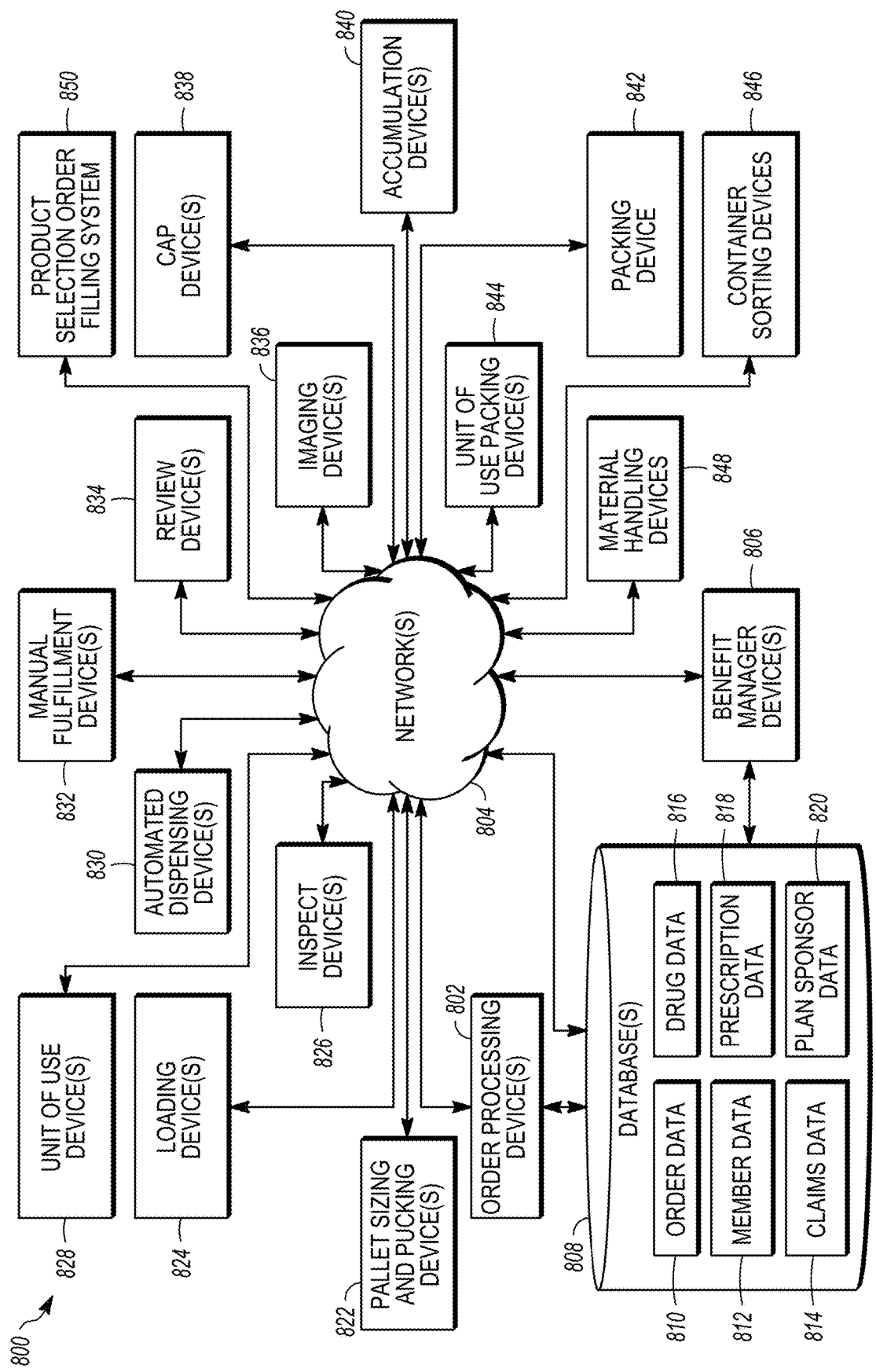
FIG. 8 illustrates a block diagram of an embodiment of a pharmacy order processing system, in accordance with the disclosed embodiments.

FIG. 8 shows a schematic view of an automated fulfillment center as an automated pharmacy 800. An automated pharmacy can be a mail order pharmacy that provides a convenient and cost-effective option for patients to receive prescription drugs. For example, a mail order pharmacy can be capable of taking advantage of economies of scale, volume dispensing of prescription drugs, and centralized warehousing and shipping to reduce the cost of prescription drugs purchased by patients of the mail order pharmacy. Some types of prescription drugs can have temperature-related storage and handling requirements in order to maintain the safety and efficacy of the drugs.

Example systems and methods for filling drug orders including an environmentally controlled drug, for example, in an automated pharmacy, are described. These pharmacies can take into account events that may interrupt delivery of the perishable items, e.g., a drug, after it leaves the pharmacy.

Generally, a prescription order is generated for an automated pharmacy, which can be a specialty pharmacy or a high-volume pharmacy. A high-volume pharmacy dispenses prescription drugs in a high volume. A high-volume pharmacy can include automatic pill dispensing systems to carry out the dispensing of the prescription drugs automatically at a rapid rate. A specialty pharmacy focuses on high cost, high touch medication therapy for patients with complex disease states. Medications in a specialty pharmacy range from oral to cutting edge injectable and biologic products. In each of these pharmacies, a drug can require environmental control while in storage and during shipping. The prescription order can include more than one prescription drug for fulfillment.

Each prescription drug in a prescription order is an order component of the prescription order. Generally, the order components are pill bottles; liquid bottles; blister packs; unit-of-use packs or products; injectable packages; spray bottles; tubes; ampoules; drop counters; insulated boxes; child-resistant containers; or other packaging having a quantity of a prescription drug contained therein. At least one of the drugs in an order can require a controlled environment. An example of a controlled environment is one that maintains a required temperature range and/or humidity range. The controlled environment can be a lowered temperature. By way of example, certain insulin needs to be stored at a temperature less than room temperature, for example at less than 32 degrees Fahrenheit (32° F.).

The prescription drugs can be dispensed at various sections of the automated pharmacy, e.g., a high-volume pharmacy or a specialty pharmacy. Some prescription orders can require manual handling of certain order components. Some prescription order components can be filled automatically by filling machinery. It is one goal of the present disclosure to provide an automated system to fill prescription orders that include an environmentally controlled drug. The system can include at least two robots to retrieve, package, and prepare for shipping the prescription order with an environmentally controlled drug.

One example of a drug that requires temperature control is HUMIRA® (adalimumab), which can be supplied as a unit-of-use product, e.g., in prefilled syringes as a preservative-free, sterile solution for subcutaneous administration. There are various unit-of-use products or packages of Humira®. For example, one unit of use product of Humira® is a package containing a pen carton containing two alcohol preps, two dose trays, six alcohol preps, and six dose trays (or other numbers of dose trays). Each dose tray consists of a single-use pen, containing a 1 mL prefilled glass syringe with a fixed 27-gauge ½ inch needle, providing 40 mg (0.8 mL) of HUMIRA®. Like many drugs, HUMIRA® must be refrigerated, e.g., at 36° F. to 46° F. (2° C. to 8° C.) and not be frozen, e.g., a temperature above 32° F. (0° C.).

A drug that requires temperature control cannot be used if it falls outside of its exclusion time period or violates its thermal budget limit during delivery. A delay of delivery can have a drug item fall outside its exclusion time period or its thermal budget limit. The exclusion time period is the time a drug can be outside of its environmental control and remain a useable drug. The exclusion time period can be a function of the time outside the environmental control and the magnitude of the change outside of the environmental control. In the case of a temperature-controlled drug, the exclusion time period can be function of time and the temperature difference between the controlled environment and the non-controlled environment. In the case of drugs, the pharmacist can set the exclusion time period. A temperature-controlled drug can have a storage temperature range for a specific time period, which can be zero seconds, less than one minute, less than two minutes, or less than five minutes. If a drug becomes frozen, then it typically cannot be thawed and used. When shipping or traveling with a temperature-controlled drug (for example, HUMIRA®) it must be stored in a shipping container that includes a cooler, which could be in the form of an ice pack or another thermally controlled carrier, to maintain the drug in the predetermined temperature range until the drug reaches its destination. Additionally, some drugs must be protected from direct sunlight, during storage and transport.

Another drug that requires environmental control is ENBREL®, which is stored between 36° F. and 46° F. (2° C. and 8° C.). This is the standard temperature for many home refrigerators. However, you can keep ENBREL® at room temperature (between 68° F. and 77° F., or 20° C. and 25° C.) for up to 14 days. Storing ENBREL® at room temperature in an automated pharmacy is not standard practice.

Other temperature-controlled drugs (including both prescription and over the counter drugs) can require different temperature ranges than ENBREL® or HUMIRA®, and the present disclosure is not limited just to these two exemplary medications. The present system can store the drugs at their required temperature ranges by storing the drugs, for example, in different cooler packages or in different zones of a single cooler package. The refrigerated cooler that stores the medication at the pharmacy also stores the medications in the required temperature ranges. It is within the scope of the present disclosure to store drugs and order components (such as sharps packages and instructions) and fill to orders with those drugs and order components along with a coolant to maintain the drugs in their required temperature ranges during shipping using the system and methods described herein.

Referencing FIG. 8 again, it illustrates, by way of example and not limitation, a block diagram of an embodiment of a pharmacy order processing system. While the system 800 is generally described as being deployed in a high-volume fulfillment center (e.g., a mail order pharmacy, a direct delivery pharmacy, a home delivery pharmacy and the like), the system 800 and/or components thereof may otherwise be deployed. The system 800 may include an order processing device 802 configured to communicate over a network 804 with a benefit manager device 806. Additional devices which may communicate over the network 804 with the benefit manager device 806 and/or the order processing device 802 may include at least some of: database(s) 808 which may store one or more than one of order data 810, member data 812, claims data 814, drug data 816, prescription data 818, and plan sponsor data 820; pallet sizing and pucking device(s) 822 (or other cart-like devices used to transport product); loading device(s) 824; inspect device(s) 826; unit-of-use device(s) 828; automated dispensing device(s) 830; manual fulfillment device(s) 832; review device(s) 834; imaging device(s) 836; cap device(s) 838; accumulation device(s) 840; packing device(s) 842; unit-of-use packing device(s) 844, container sorting device(s) 846 configured to image and sort containers, material handlings devices 848 configured to transport the containers throughout the system 800, and a product selection order filling system 850 configured to fill daily dosage unit pharmacy orders. The system 800 may also include additional devices. The system 800 can compute likely delivery delays using GIS information or other geospatial data.

The order processing device 802 may receive information about prescriptions being filled at a pharmacy in which the order processing device 802 is deployed. In general, the order processing device 802 may be a device located within or otherwise associated with a pharmacy location to enable fulfillment of a prescription by dispensing prescription drugs. In some embodiments, the order processing device 802 may be a device separate from a pharmacy that enables communication with other devices located within a pharmacy. For example, the order processing device 802 may be in communication with another order processing device 802 and/or other devices located with a pharmacy. In some embodiments, an external pharmacy order processing device 802 may have limited functionality (e.g., as operated by a patient requesting fulfillment of a prescription drug) when an internal pharmacy order processing device 802 may have greater functionality (e.g., as operated by a pharmacy).

The order processing device 802 can conduct the processing of the geospatial information to determine if there are likely delays in delivery. If delays are predicted in the case of models or determined based on processing, the order processing device 802 can remove orders from processing on the devices described herein for fulfilling an order. The order processing device 802 can place the removed orders to a hold queue or flagged in the order database for not-filling with a select fulfillment cycle. The orders in the hold queue can be reintegrated into a subsequent order processing, e.g., after a predicted time period or when a carrier indicates that it can resume on-time deliveries in a region of interest.

The order processing device 802, after the checking for delivery delays, may track a pharmaceutical order as it is fulfilled. A pharmaceutical order may include a prescription order for prescription medicine as well as may include non-prescription medicine and/or non-medical products. A prescription order may include one or more than one prescription to be filled by the pharmacy. The order processing device 802 may make pharmacy routing decisions and/or order consolidation decisions for a prescription order. The pharmacy routing decisions may include what device or devices in the pharmacy are responsible for filling at least a portion of the pharmaceutical order, where the order consolidation decisions include whether portions of a pharmaceutical order or multiple pharmaceutical orders should be shipped together for a patient or a patient family. The order processing device 802 may operate in combination with the benefit manager device 806.

Examples of the order processing device 802 may include a processor operably connected to a memory storing instructions for order fulfillment; however other devices may also be used. For example, the order processing device 802 may include a mobile electronic device. The order processing device 802 may include other computing devices, such as desktop computing devices, notebook computing devices, netbook computing devices, gaming devices, and the like, which when loaded with instructions to determine delivery delay are dedicated machines. The device 802 may include a processor, a memory to store data and instructions, and communication functionality. Other types of electronic devices that can use rules and instructions to execute various functions may also be used.

Examples of the network 804 include Mobile Communications (GSM) network, a code division multiple access (CDMA) network, 3rd Generation Partnership Project (3GPP), an Internet Protocol (IP) network, a Wireless Application Protocol (WAP) network, a WiFi network, or an IEEE 802.11 standards network, as well as various combinations thereof. The network 804 may include optical communications. The network 804 may be a local area network or a global communication network, such as the Internet. Other conventional and/or later developed wired and wireless networks may also be used. In some embodiments, the network 804 may include a prescribing network such as the electronic prescribing network operated by Surescripts of Arlington, Virginia.

The benefit manager device 806 may be operated by an entity at least partially responsible for creation and/or management of the pharmacy or drug benefit. The benefit manager operating the benefit manager device 806 may be a pharmacy benefit manager (PBM), or may be other entities that operate the benefit manager device 806 either on behalf of themselves, the PBM, or another entity. For example, the benefit manager may be operated by a health plan, a retail pharmacy chain, a drug wholesaler, a data analytics or other type of software-related company, or the like. In some embodiments, a PBM that provides the pharmacy benefit may also provide one or more than one additional benefits including a health benefit, a dental benefit, a vision benefit, a wellness benefit, a radiology benefit, a pet care benefit, an insurance benefit, a long term care benefit, a nursing home benefit, and the like. The PBM may, in addition to its PBM operations, operate one or more than one pharmacy. The pharmacies may be retail pharmacies, mail order pharmacies, etc.

By way of example and not limitation, a member (or a person on behalf of the member) of a pharmacy benefit plan administered by or through the PBM may attempt to obtain a prescription drug at a retail pharmacy location where the member can obtain drugs in a physical store from a pharmacist or pharmacist technician, or in some instances through mail order drug delivery from a mail order pharmacy location. The member may obtain a prescription drug directly or indirectly through the use of a machine, such as a kiosk, vending unit, mobile electronic device, or a different type of mechanical, electrical, an electronic communication device and/or computing device.

The member may have a co-pay for the prescription drug that reflects an amount of money that the member is responsible to pay the pharmacy for the prescription drug. The money paid by the member to the pharmacy may come from the personal funds of the member, a health savings account (HSA) of the member or the member's family, a health reimbursement arrangement (HRA) of the member or the member's family, a flexible spending accounts (FSA) of the member or the member's family, or the like. An employer of the member may directly or indirectly fund or reimburse the member or an account of the member for the co-pay.

The amount of the co-pay paid by the member may vary by the benefit plan of a plan sponsor or client with the PBM. The member's co-pay may be based on a flat co-pay (e.g., $10), co-insurance (e.g., 10%), and/or a deductible (e.g., for first $500 of annual prescription drug spend) for certain prescription drugs, certain types of prescription drugs, and/or all prescription drugs. In certain instances, the member may not pay the co-pay or may only pay for a portion of a co-pay for a prescription drug. For example, if the usual and customary cost for a generic version of a prescription drug is $4, and the member's flat co-pay is $20 for the prescription drug, the member may only pay $4 to receive the prescription drug. In another example involving a worker's compensation claim, no co-pay may be due by the member for the prescription drug. The co-pay may also vary based on the channel used to receive the prescription drug. For example, the co-pay for receiving prescription drugs from a mail order pharmacy location may be less than the co-pay for receiving prescription drugs from a retail pharmacy location.

In conjunction with receiving the co-pay (if any) from the member and dispensing the prescription drug to the member, the pharmacy submits a claim to the PBM for the prescription drug. The PBM may perform certain adjudication operations including verifying the eligibility of the member, reviewing the formulary of the member to determine appropriate co-pay, coinsurance, and deductible for the prescription drug, and performing a drug utilization review (DUR) on the member. The PBM then provides a response to the pharmacy following performance of at least some of the aforementioned operations. As part of the adjudication, the plan sponsor (or the PBM on behalf of the plan sponsor) ultimately reimburses the pharmacy for filling the prescription drug when the prescription drug was successfully adjudicated. The aforementioned adjudication operations generally occur before the co-pay is received and the prescription drug dispensed. However, the operations may occur simultaneously, substantially simultaneously, or in a different order. In addition, more or less adjudication operations may be performed as at least part of the adjudication process.

The amount of reimbursement paid to the pharmacy by a plan sponsor and/or money paid by the member may be based at least in part on the type of pharmacy network in which the pharmacy is included. Other factors may be used to determine the amount in addition to the type of pharmacy network. For example, if the member pays the pharmacy for the prescription without using the prescription drug benefit provided by the benefit manager, the amount of money paid by the member may be higher and the amount of money received by the pharmacy for dispensing the prescription drug and for the prescription drug itself may be higher. Some or all of the foregoing operations may be performed by executing instructions on the benefit manager device 806 and/or an additional device.

In some embodiments, at least some of the functionality of the order processing device 802 may be included in the benefit manager device 806. The order processing device 802 may be in a client-server relationship with the benefit manager device 806, a peer-to-peer relationship with the benefit manager device 806, or in a different type of relationship with the benefit manager device 806.

The order processing device 802 and/or the benefit manager device 806 may be in communication directly (e.g., through local storage) and/or through the network 804 (e.g., in a cloud configuration or software as a service) with a database 808 (e.g., as may be retained in memory or otherwise). The database 808 may store order data 810, member data 812, claims data 814, drug data 816, prescription data 818, and/or plan sponsor data 820. Other data may be stored in the database 808.

The order data 810 may include data related to the order of prescriptions including the type (e.g., drug name and strength) and quantity of each prescription in a prescription order. The order data 810 may also include data used for completion of the prescription, such as prescription materials. Prescription materials may be a type of order materials that include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, or the like. The order data 810 may be used by a high-volume fulfillment center to fulfill a pharmacy order.

In some embodiments, the order data 810 may include verification information associated with fulfillment of the prescription in the pharmacy. For example, the order data 810 may include videos and/or images taken of: the prescription drug prior to dispensing, during dispensing, and/or after dispensing; a prescription container (e.g., a prescription bottle and sealing lid) used to contain the prescription drug prior to dispensing, during dispensing, and/or after dispensing; the packaging and/or packaging materials used to ship or otherwise deliver the prescription drug prior to dispensing, during dispensing, and/or after dispensing; and/or the fulfillment process within the pharmacy. Other type of verification information such as bar code data read from pallets used to transport prescriptions within the pharmacy may also be stored as order data 810.

The member data 812 includes information regarding the members associated with the benefit manager. Examples of the member data 812 include name, address, telephone number, e-mail address, prescription drug history, and the like. The member data 812 may include a plan sponsor identifier that identifies the plan sponsor associated with the member and/or a member identifier that identifies the member to the plan sponsor. The member data 812 may include a member identifier that identifies the plan sponsor associated with the patient and/or a patient identifier that identifies the patient to the plan sponsor. The member data 812 may also include, by way of example, dispensation preferences such as type of label, type of cap, message preferences, language preferences, or the like.

The member data 812 may be accessed by various devices in the pharmacy, e.g., the high-volume fulfillment center, to obtain information utilized for fulfillment and shipping of prescription orders. In some embodiments, an external order processing device 802 operated by or on behalf of a member may have access to at least a portion of the member data 812 for review, verification, or other purposes.

In some embodiments, the member data 812 may include information for persons who are patients of the pharmacy but are not members in a benefit plan being provided by the benefit manager. For example, these patients may obtain drug directly from the pharmacy, through a private label service offered by the pharmacy, the high-volume fulfillment center, or otherwise. In general, the use of the terms member and patient may be used interchangeably herein.

The claims data 814 includes information regarding pharmacy claims adjudicated by the PBM under a drug benefit program provided by the PBM for one, or more than one, plan sponsors. In general, the claims data 814 includes an identification of the client that sponsors the drug benefit program under which the claim is made, and/or the member that purchased the prescription drug giving rise to the claim, the prescription drug that was filled by the pharmacy (e.g., the national drug code number), the dispensing date, generic indicator, GPI number, medication class, the cost of the prescription drug provided under the drug benefit program, the copay/coinsurance amount, rebate information, and/or member eligibility. Additional information may be included.

In some embodiments, other types of claims beyond prescription drug claims may be stored in the claims data 814. For example, medical claims, dental claims, wellness claims, or other type of health care-related claims for members may be stored as a portion of the claims data 814.

In some embodiments, the claims data 814 includes claims that identify the members with whom the claims are associated. In some embodiments, the claims data 814 includes claims that have been de-identified (e.g., associated with a unique identifier but not with a particular, identifiable member).

The drug data 816 may include drug name (e.g., technical name and/or common name), other names by which the drug is known by, active ingredients, an image of the drug (e.g., in pill form), and the like. The drug data 816 may include information associated with a single medication or multiple medications.

The prescription data 818 may include information regarding prescriptions that may be issued by prescribers on behalf of patients, who may be members of the drug benefit plan, for example to be filled by a pharmacy. Examples of the prescription data 818 include patient names, medication or treatment (such as lab tests), dosing information, and the like. The prescriptions may be electronic prescriptions, paper prescriptions that have been scanned, or otherwise. In some embodiments, the dosing information reflects a frequency of use (e.g., once a day, twice a day, before each meal, etc.) and a duration of use (e.g., a few days, a week, a few weeks, a month, etc.).

In some embodiments, the order data 810 may be linked to associated member data 812, claims data 814, drug data 816, and/or prescription data 818.

The plan sponsor data 820 includes information regarding the plan sponsors of the benefit manager. Examples of the plan sponsor data 820 include company name, company address, contact name, contact telephone number, contact e-mail address, and the like.

The order processing device 802 may direct at least some of the operations of the devices illustrated in FIG. 8. In some embodiments, operations performed by one of these devices may be performed sequentially, or in parallel with the operations of another device as may be coordinated by the order processing device 802. In some embodiments, the order processing device 802 tracks a prescription with the pharmacy based on operations performed by one or more of the devices illustrated in FIG. 8.

A material transport system or assembly may be used to transport product. For example, conveyors may include gravity conveyors or powered conveyors. Powered conveyors may include but are not limited chain-driven conveyors, pallet conveyors and servo-controlled conveyors. Intelligent conveyor systems may be designed to control the speed and/or direction of lines of article motion, and may allow individual articles to be inserted or removed from the line. Intelligent conveyor system may be designed to enable electronic movement control of individual transport mechanisms (e.g. pucks) for the product. For example, conveyor systems may be designed with one or more servo motors, controlled by a programmable servo controller, to electronically control movement of an individual puck. An example of an intelligent system may move individual carts, with or without a puck in or otherwise connected to the cart, along rails, under electronic control, in order to enable individual articles to be inserted and/or removed from line(s) of articles. Material transport systems may include a rotating structure with a periphery. Objects may be on a surface near the periphery such that they move as the structure rotates. Other material transport systems may be used. The material transport system may include combinations different types of material transport systems, such as a combination of two or more of a gravity conveyor, a power conveyor, and an intelligent conveyor.

In some embodiments, by way of example, the system 800 may transport product such as prescription drug containers (e.g., between or among devices, such as one of more devices illustrated in FIG. 8, in the high-volume fulfillment center) by use of pallets. The pallet sizing and pucking device 822 may configure pucks in a pallet. A pallet may be a transport structure for a number of the prescription containers 801, and may include a number of cavities. A puck may be placed in one or more than one of the cavities in a pallet by the pallet sizing and pucking device 822. A puck may include a receptacle sized and shaped to receive a prescription container 801. Such containers may be supported by the pucks during carriage in the pallet. Different pucks may have differently sized and shaped receptacles to accommodate containers of differing sizes, as may be appropriate for different prescriptions.

The arrangement of pucks in a pallet may be determined by the order processing device 802 based on prescriptions which the order processing device 802 decides to launch. In general, prescription orders in the storage device 808 reside in one or more than one queues, and are generally launched in a first-in-first-out order. However, the order processing device 802 may use logic and a variety of factors to determine when and how prescriptions are to be launched. For example, some non-limiting factors which may alter the first-in-first-out order of launching prescriptions in a pharmacy include the age of the order, whether the order required an outreach to a physician or some other intervention, whether there are any performance guarantees with plan sponsors or members, the available inventory of a given pharmaceutical in view of existing prescriptions already launched which will require that pharmaceutical, the zip code to which the order will be shipped, the workload and volume of various parts of the pharmacy, whether valid paperwork for the order has been received, and/or similar orders for the same pharmaceutical that are already to be launched. The logic may be implemented directly in the pallet sizing and pucking device 822, in the order processing device 802, in both devices 802, 822, or otherwise. Once a prescription is set to be launched, a puck suitable for the appropriate size of container for that prescription may be positioned in a pallet by a robotic arm or pickers. The pallet sizing and pucking device 822 may launch a pallet once pucks have been configured in the pallet.

The loading device 824 may load prescription containers into the pucks on a pallet by a robotic arm, pick and place mechanism, or the like. In one embodiment, the loading device 808 has robotic arms or pickers to grasp a prescription container and move it to and from a pallet or a puck. The loading device 824 may also print a label, which is appropriate for a container that is to be loaded onto the pallet, and apply the label to the container 801. The pallet may be located on a conveyor assembly during these operations, e.g., at the high-volume fulfillment center.

The inspect device 826 may verify that containers are correctly labeled and positioned on a material transport system. For example, the inspect device 826 may verify that containers in a pallet are in correct spots on the pallet. The inspect device 826 may scan the label on one or more than one container on the pallet. Labels of the containers may be scanned or imaged in full or in part by the inspect device 826. Such imaging may occur after the container has been lifted out of its puck by a robotic arm, picker, or the like, or may be otherwise scanned or imaged while retained in the puck. In some embodiments, images and/or video captured by the inspect device 826 may be stored in the database 808 as order data 810.

The unit-of-use device 828 may temporarily store, monitor, label and/or dispense unit-of-use products. In general, unit-of-use products are prescription drug products that may be delivered to a patient or member without being repackaged at the pharmacy. These products may include pills in a container 801, pills in a blister pack, inhalers, and the like. Prescription drug products dispensed by the unit-of-use device 828 in their original packaging may be packaged individually or collectively for shipping, or may be shipped in combination with other prescription drugs dispenses by other devices in the high-volume fulfillment center.

The automated dispensing device 830 may include one or more than one device that dispense prescription drugs or pharmaceuticals into prescription containers in accordance with one or multiple prescription orders. In general, the automated dispensing device 830 may include mechanical and electronic components with, in some embodiments, software and/or logic to facilitate pharmaceutical dispensing that would otherwise be performed in a manual fashion by a pharmacist and/or pharmacist technician. For example, the automated dispensing device 830 may include high-volume fillers that fill a number of prescription drug types at a rapid rate and blister pack machines that dispense and pack drugs into a blister pack. Prescription drugs dispensed by the automated dispensing devices 830 may be packaged individually or collectively for shipping, or may be shipped in combination with other prescription drugs dispenses by other devices in the high-volume fulfillment center.

The manual fulfillment device 832 may provide for manually fulfillment of prescriptions. For example, the manual fulfillment device 832 may receive or obtain a container and enable fulfillment of the container by a pharmacist or pharmacy technician. In some embodiments, the manual fulfillment device 832 provides the filled container to another device in the system 800 to be joined with other containers in a prescription order for a patient or member. In general, a manual fulfillment may include operations at least partially performed by a pharmacist or pharmacy technician. For example, a person may retrieve a supply of the prescribed drug, may make an observation, may count out a prescribed quantity of drugs and place them into a prescription container 801, or the like. Some portions of the manual fulfillment process may be automated by use of a machine. For example, counting of capsules, tablets, or pills (types of drug delivery structures) may be at least partially automated (e.g., through use of a pill counter). Prescription drugs dispensed by the manual fulfillment device 832 may be packaged individually or collectively for shipping, or may be shipped in combination with other prescription drugs dispenses by other devices in the high-volume fulfillment center.

The review device 834 may process prescription containers to be reviewed by a pharmacist for proper pill count, exception handling, prescription verification, and the like. Fulfilled prescriptions may be manually reviewed and/or verified by a pharmacist, as may be required by state or local law. A pharmacist or other licensed pharmacy person who may dispense certain drugs in compliance with local and/or other laws may operate the review device 834 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been cancelled, containers with defects, and the like.

The imaging device 836 may image containers once they have been filled with pharmaceuticals. The imaging device 836 may measure the fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 802, and/or stored in the database 810 as part of the order data 810.

The cap device 838 may be used to cap or otherwise seal a prescription container 801. In some embodiments, the cap device 838 may secure a prescription container with a type of cap in accordance with a patient preference (e.g., a preference regarding child resistance), a plan sponsor preference, a prescriber preference, or the like. The cap device 838 may also etch a message into the cap, although this process may be performed by a subsequent device in the high-volume fulfillment center. The cap may include an induction liner. After the cap with the induction liner is placed on the container, an induction sealer may heat the induction liner such that the induction liner forms a tamper-evident seal over the container.

The accumulation device 840 may be used to accumulate containers, including one or more types of containers, of prescription drugs in a prescription order. The accumulation device 840 may accumulate prescription containers from various devices or areas of the pharmacy. For example, the accumulation device 840 may accumulate prescription containers from the unit-of-use device 828, the automated dispensing device 830, the manual fulfillment device 832, and the review device 834, at the high-volume fulfillment center. The accumulation device 840 may be used to group the prescription containers prior to shipment to the member or otherwise.

The packing device 842 may be configured to package a prescription order in preparation for shipping the order. For example, the packing device 842 may box, bag, or otherwise package the fulfilled prescription order for delivery. The packing device 842 may further place inserts into the packaging. For example, bulk prescription orders may be shipped in a box, while other prescription orders may be shipped in a bag which may be a wrap seal bag. The packing device 842 may label the box or bag with the address and a recipient's name. The packing device 842 may sort the box or bag for mailing in an efficient manner (e.g., sort by delivery address). The packing device 842 may include ice or temperature sensitive elements for prescriptions which are to be kept within a temperature range during shipping in order to retain efficacy or otherwise. The package may then be shipped through postal mail, through a mail order delivery service that ships via group and/or air (e.g., UPS, FedEx, or DHL), through delivery service, through a locker box at a shipping site (e.g., Amazon locker or a PO Box), or otherwise.

The unit-of-use packing device 844 may be configured to package a unit-of-use prescription order in preparation for shipping the order. The unit-of-use packing device 844 may include manual scanning of containers to be bagged for shipping to verify each container in the order.

The devices illustrated in FIG. 8 may be separate device or combined. When multiple devices are present, the multiple devices may be of the same device type or models or may be a different device type or model.

Moreover, the system 800 shows a single network 804; however, multiple networks can be used. The multiple networks may communicate in series with each other to link the devices or in parallel to link the devices. Multiple devices may share processing and/or memory resources. The devices may be located in the same area or in different locations. For example, the devices may be located in a building or set of adjoining buildings. They may be interconnected (e.g. by conveyors), networked, and/or otherwise in contact with one another or integrated with one another, e.g., at the high-volume fulfillment center. In addition, the functionality of a device may be split among a number of discrete devices and/or combined with other devices.

If the order processing device 802 determines that an order should not be filled during the current fulfillment cycle, then the other devices need not be engaged or operated delayed orders.

The geospacial systems and methods described herein can provide be used to develop predictive models of when environmentally controlled items can be packaged and shipped to recipients. Operations as described herein for use in the various embodiments can start with a component of the system accessing data related to a delivery location and items to be delivered. The possible delivery locations can be a domicile, medical care facilities, doctor offices, pharmacies or the like. In an example, the home of the user, who may be associated with the mobile device, is set a possible location for the geofence. The home location can be the delivery site of medicines and prescriptions using a home delivery option. An example of home delivery of medications can be found in U.S. Pat. Nos. 6,769,228, 7,430,838, 8,706,522, and 10,325,333, which are each hereby incorporated by reference. In an example embodiment, the home location of the user associated with the mobile device, medical appointment or prescription is included.

If the weather or other disruptive event has a significant location change, the system can recalculate the possible delivery locations and the disrupted delivery locations. These locations can be identified by various geographic boundaries. One example boundary is postal code, e.g., zip code. Another example of a geographic boundary is distance from a delivery hub, e.g., a minimum distance (e.g., radius), that a package can be delivered before an adverse event occurs. The distance from a delivery hub can be the distance traveled on a roadway. The minimum distance can be a timed event, e.g., a time for a delivery vehicle to leave a hub, deliver package and return to the hub. The delivery boundaries can also be modified based on predicted or known flood areas. The system can recalculate the map display to show delivery and non-delivery locations on an electronic device display.

Accordingly, the embodiments described herein provide geographic based alerts to healthcare applications to assist customers/patients and the fulfillment center in managing the healthcare, medication and any other related items. The geographic based alerts can advise recipient related to filling of a prescription. The alert may be varied based on the location of the recipient, the events, customer/patient data, the type of prescription to be filled, and other third party data. The alert can trigger a fulfillment system to not fill certain orders. The alert may have a time limitation, e.g., do not fill that day. The fulfillment center will then place the delayed order to the que after the time limitation, e.g., next day. The time limitation can be set at a day or multiple days. The time limitation can be dynamic and computed by the predictive model based on the events being fed into the model. The alert can be sent over communication networks, e.g., packet based systems, intranets, global computer networks. Further modifications to the alerts may become apparent to those skilled in the art based on the description provided herein.

Hardware Diagrams

The technology discussed herein makes reference to computing devices, databases, software applications, and other computer-based systems, as well as actions taken and information sent to and from such systems. One of ordinary skill in the art will recognize that the inherent flexibility of computer-based systems allows for a great variety of possible configurations, combinations, and divisions of tasks and functionality between and among components. For instance, computer-implemented processes discussed herein can be implemented using a single computing device or multiple computing devices working in combination. Databases and applications can be implemented on a single system or distributed across multiple systems. Distributed components can operate sequentially or in parallel. Such configurations can be implemented without deviating from the scope of the present disclosure. The technology described herein can generate the data sets for use in the delivery delay predictive model and execute the predictive model itself. The technology can also be used to flag a specific region with orders that should delay fulfillment and leave the fulfillment center. In an example embodiment the predictive model can send an alert or set a flag in a table to be received by or access by the pharmacy system 800 or order processing device 802, which will then determine the orders to not be filled until the alert ends or the flag is removed.

Figure 9:
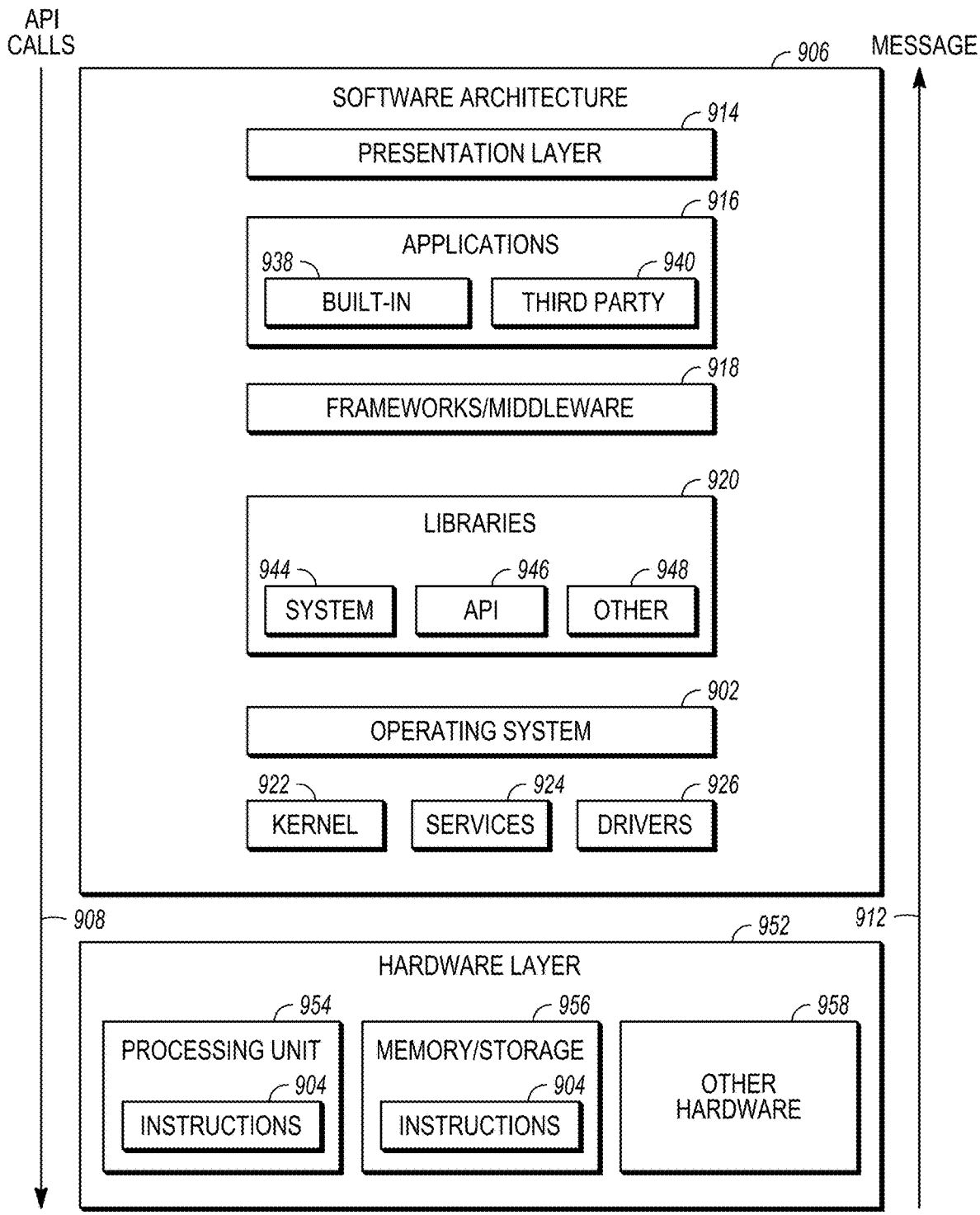
FIG. 9 is a block diagram illustrating an example software architecture that may be used in conjunction with various hardware architectures described herein, in accordance with the disclosed embodiments.

FIG. 9 is a block diagram illustrating an example software architecture 906, which may be used in conjunction with various hardware architectures herein described. FIG. 9 is a non-limiting example of a software architecture and it will be appreciated that many other architectures may be implemented to facilitate the functionality described herein. The software architecture 906 may execute on hardware such as machine 1000 of FIG. 10 that includes, among other things, processors 1004, memory 1006, and input/output (I/O) components 1018. A representative hardware layer 952 is illustrated and can represent, for example, the machine 1000 of FIG. 10. The representative hardware layer 952 includes a processing unit 954 having associated executable instructions 904. Executable instructions 904 represent the executable instructions of the software architecture 906, including implementation of the methods, components, and so forth described herein. The instructions can provide a framework for gathering, managing, and analyzing data. The instructions can analyze spatial location and organizes layers of information into visualizations using maps and three dimensional scenes. The present instructions can reveal insights into the data, such as patterns, relationships, and situations. The instructions can assist the fulfillment center in alter prescription delivery. The hardware layer 952 also includes memory and/or storage devices 956, which also have executable instructions 904. The hardware layer 952 may also comprise other hardware 958. The software architecture 906 may be deployed in any one or more than one of the components shown in FIGS. 1-8. For example, the software architecture 906 can be utilized to generate the geofences, alerts, and reports as described herein.

In the example architecture of FIG. 9, the software architecture 906 may be conceptualized as a stack of layers where each layer provides particular functionality. For example, the software architecture 906 may include layers such as an operating system 902, libraries 920, frameworks/middleware 918, applications 916, and a presentation layer 914. Operationally, the applications 916 and/or other components within the layers may invoke API calls 908 through the software stack and receive messages 912 in response to the API calls 908. The layers illustrated are representative in nature and not all software architectures have all layers. For example, some mobile or special purpose operating systems may not provide a frameworks/middleware 918, while others may provide such a layer. Other software architectures may include additional or different layers.

The operating system 902 may manage hardware resources and provide common services. The operating system 902 may include, for example, a kernel 922, services 924, and drivers 926. The kernel 922 may act as an abstraction layer between the hardware and the other software layers. For example, the kernel 922 may be responsible for memory management, processor management (e.g., scheduling), component management, networking, security settings, and so on. The services 924 may provide other common services for the other software layers. The drivers 926 are responsible for controlling or interfacing with the underlying hardware. For instance, the drivers 926 include display drivers, camera drivers, Bluetooth® drivers, flash memory drivers, serial communication drivers (e.g., Universal Serial Bus (USB) drivers), WI-FT® drivers, audio drivers, power management drivers, and so forth, depending on the hardware configuration.

The libraries 920 provide a common infrastructure that is used by the applications 916 and/or other components and/or layers. The libraries 920 provide functionality that allows other software components to perform tasks in an easier fashion than to interface directly with the underlying operating system 902 functionality (e.g., kernel 922, services 924 and/or drivers 926). The libraries 920 may include system libraries 944 (e.g., C standard library) that may provide functions such as memory allocation functions, string manipulation functions, mathematical functions, and the like. In addition, the libraries 920 may include API libraries 946 such as media libraries (e.g., libraries to support presentation and manipulation of various media format such as MPREG4, H.264, MP3, AAC, AMR, JPG, PNG), graphics libraries (e.g., an OpenGL framework that may be used to render two-dimensional and three-dimensional in a graphic content on a display), database libraries (e.g., SQLite that may provide various relational database functions), web libraries (e.g., WebKit that may provide web browsing functionality), and the like. The libraries 920 also may include a wide variety of other libraries 948 to provide many other APIs to the applications 916 and other software components/devices.

The frameworks/middleware 918 (also sometimes referred to as middleware) provide a higher-level common infrastructure that may be used by the applications 916 and/or other software components/devices. For example, the frameworks/middleware 918 may provide various graphic user interface functions, high-level resource management, high-level location services, and so forth. The frameworks/middleware 918 may provide a broad spectrum of other APIs that may be utilized by the applications 916 and/or other software components/devices, some of which may be specific to a particular operating system 902 or platform.

The applications 916 can include built-in applications 938 and/or third-party applications 940. The applications can generate the data sets for the overlay operations. The applications can execute the predictive model. Examples of representative built-in applications 938 may include, but are not limited to, a contacts application, a browser application, a book reader application, a location application, a media application, a messaging application, and/or a game application. Third-party applications 940 may include an application developed using the ANDROID™ or IOS™ software development kit (SDK) by an entity other than the vendor of the particular platform, and may be mobile software running on a mobile operating system such as IOS™, ANDROID™ WINDOWS® Phone, or other mobile operating systems. The third-party applications 940 may invoke the API calls 908 provided by the mobile operating system (such as operating system 902) to facilitate the functionality described herein.

The applications 916 may use built-in operating system functions (e.g., kernel 922, services 924, and/or drivers 926), libraries 920, and frameworks/middleware 918 to create UIs to interact with users of the system. Alternatively, or additionally, in some systems, interactions with a user may occur through a presentation layer, such as presentation layer 914. In these systems, the application/component "logic" can be separated from the aspects of the application/component that interact with a user.

Figure 10:
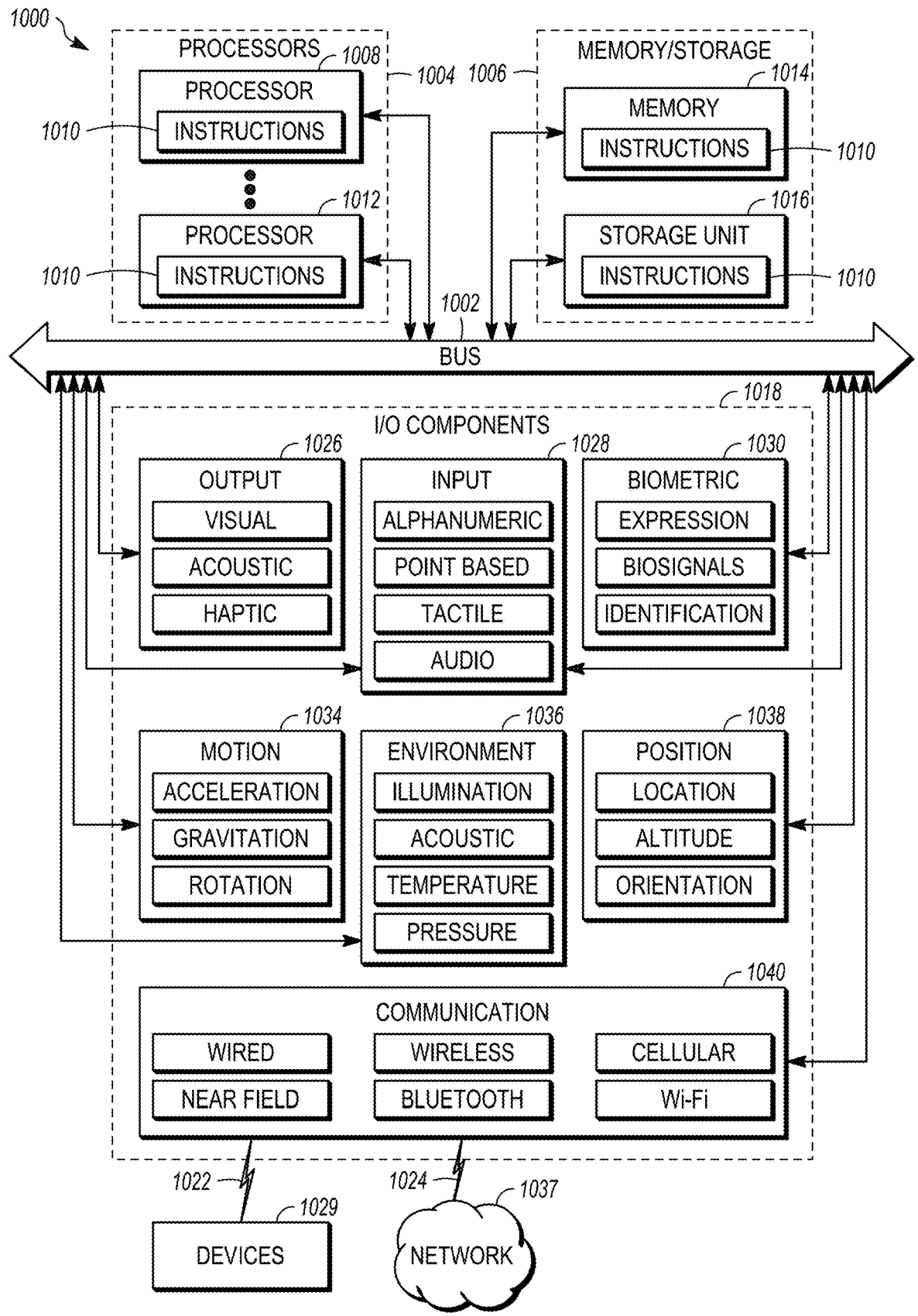
FIG. 10 is a block diagram illustrating components of a computer system, in accordance with the disclosed embodiments.

FIG. 10 is a block diagram illustrating components of a machine 1000, according to some example embodiments, able to read instructions from a machine-readable medium (e.g., a machine-readable storage medium) and to perform any one or more of the methodologies discussed herein. Specifically, FIG. 10 shows a diagrammatic representation of the machine 1000 in the example form of a computer system, within which instructions 1010 (e.g., software, a program, an application, an applet, an app, or other executable code) for causing the machine 1000 to perform any one or more of the methodologies discussed herein may be executed. For example, the instructions 1010 may be executed by the mobile user device 100 to implement the geofences, alerts, and report functions as described herein.

As such, the instructions 1010 may be used to implement the devices or components described herein. The instructions 1010 transform the general, non-programmed machine 1000 into a particular machine 1000 programmed to carry out the described and illustrated functions in the manner described. In alternative embodiments, the machine 1000 operates as a standalone device or may be coupled (e.g., networked) to other machines. In a networked deployment, the machine 1000 may operate in the capacity of a server machine or a client machine in a server-client network environment, or as a peer machine in a peer-to-peer (or distributed) network environment. The machine 1000 may comprise, but not be limited to, a server computer, a client computer, a personal computer (PC), a tablet computer, a laptop computer, a netbook, a STB, a PDA, an entertainment media system, a cellular telephone, a smartphone, a mobile device, a wearable device (e.g., a smart watch), a smart home device (e.g., a smart appliance), other smart devices, a web appliance, a network router, a network switch, a network bridge, or any machine capable of executing the instructions 1010, sequentially or otherwise, that specify actions to be taken by machine 1000. Further, while only a single machine 1000 is illustrated, the term "machine" shall also be taken to include a collection of machines that individually or jointly execute the instructions 1010 to perform any one or more of the methodologies discussed herein.

The machine 1000 may include processors 1004, memory 1006, and I/O components 1018, which may be configured to communicate with each other such as via a bus 1002. In an example embodiment, the processors 1004 (e.g., a central processing unit (CPU), a reduced instruction set computing (RISC) processor, a complex instruction set computing (CISC) processor, a graphics processing unit (GPU), a digital signal processor (DSP), an application-specific integrated circuit (ASIC), a radio-frequency integrated circuit (RFIC), another processor, or any suitable combination thereof) may include, for example, a processor 1008 and a processor 1012 that may execute the instructions 1010. The term "processor" is intended to include multi-core processors 1004 that may comprise two or more independent processors (sometimes referred to as "cores") that may execute instructions contemporaneously. Although FIG. 10 shows multiple processors 1004, the machine 1000 may include a single processor with a single core, a single processor with multiple cores (e.g., a multi-core processor), multiple processors with a single core, multiple processors with multiple cores, or any combination thereof.

The memory 1006 may include a memory 1014, such as a main memory, or other memory storage, and a storage unit 1016, both accessible to the processors 1004 such as via the bus 1002. The storage unit 1016 and memory 1014 store the instructions 1010 embodying any one or more of the methodologies or functions described herein. The instructions 1010 may also reside, completely or partially, within the memory 1014, within the storage unit 1016, within at least one of the processors 1004 (e.g., within the processor's cache memory), or any suitable combination thereof, during execution thereof by the machine 1000. Accordingly, the memory 1014, the storage unit 1016, and the memory of processors 1004 are examples of machine-readable media.

The I/O components 1018 may include a wide variety of components to receive input, provide output, produce output, transmit information, exchange information, capture measurements, and so on. The specific I/O components 1018 that are included in a particular machine 1000 will depend on the type of machine. For example, portable machines such as mobile phones will likely include a touch input device or other such input mechanisms, while a headless server machine will likely not include such a touch input device. It will be appreciated that the I/O components 1018 may include many other components that are not shown in FIG. 10. The I/O components 1018 are grouped according to functionality merely for simplifying the following discussion and the grouping is in no way limiting. In various example embodiments, the I/O components 1018 may include output components 1026 and input components 1028. The output components 1026 may include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The input components 1028 may include alphanumeric input components (e.g., a keyboard, a touch screen configured to receive alphanumeric input, a photo-optical keyboard, or other alphanumeric input components), point-based input components (e.g., a mouse, a touchpad, a trackball, a joystick, a motion sensor, or other pointing instrument), tactile input components (e.g., a physical button, a touch screen that provides location and/or force of touches or touch gestures, or other tactile input components), audio input components (e.g., a microphone), and the like.

In further example embodiments, the I/O components 1018 may include biometric components 1039, motion components 1034, environmental components 1036, or position components 1038 among a wide array of other components. For example, the biometric components 1039 may include components to detect expressions (e.g., hand expressions, facial expressions, vocal expressions, body gestures, or eye tracking), measure biosignals (e.g., blood pressure, heart rate, body temperature, perspiration, or brain waves), identify a person (e.g., voice identification, retinal identification, facial identification, fingerprint identification, or electroencephalogram based identification), and the like. The motion components 1034 may include acceleration sensor components (e.g., accelerometer), gravitation sensor components, rotation sensor components (e.g., gyroscope), and so forth. The environmental components 1036 may include, for example, illumination sensor components (e.g., photometer), temperature sensor components (e.g., one or more than one thermometer that detect ambient temperature), humidity sensor components, pressure sensor components (e.g., barometer), acoustic sensor components (e.g., one or more than one microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that may provide indications, measurements, or signals corresponding to a surrounding physical environment. The position components 1038 may include location sensor components (e.g., a satellite navigation receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 1018 may include communication components 1040 operable to couple the machine 1000 to a network 1037 or devices 1029 via coupling 1024 and coupling 1022, respectively. For example, the communication components 1040 may include a network interface component or other suitable device to interface with the network 1037. In further examples, communication components 1040 may include wired communication components, wireless communication components, cellular communication components, Near Field Communication (NFC) components, Bluetooth® components (e.g., Bluetooth® Low Energy), WI-FI® components, and other communication components to provide communication via other modalities. The devices 1029 may be another machine or any of a wide variety of peripheral devices (e.g., a peripheral device coupled via a USB).

Moreover, the communication components 1040 may detect identifiers or include components operable to detect identifiers. For example, the communication components 1040 may include Radio Frequency Identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information may be derived via the communication components 1040, such as location via Internet Protocol (IP) geolocation, location via WI-FI® signal triangulation, location via detecting a NFC beacon signal that may indicate a particular location, and so forth.

The various memories (i.e., 956, 1006 and/or memory of the processor unit(s) 954, 1004 and 1012 and/or storage unit 1016) may store one or more sets of instructions and data structures (e.g., instructions) 904 and 1010 embodying or used by any one or more of the methodologies or functions described herein. These instructions, when executed by processor unit(s) 954, 1004, and 1012 cause various operations to implement the disclosed examples. The instructions can include the predictive model instructions and the data set handling instructions.

The instructions 904 and 1010 can further be transmitted or received over a communications network 1037 using a transmission medium via the communication components 1040 using any one of a number of well-known transfer protocols (e.g., HTTP). Examples of communication networks include a LAN, a WAN, the Internet, mobile telephone networks, plain old telephone service (POTS) networks, and wireless data networks (e.g., WI-FI®, 3G, 4G LTE/LTE-A, 5G or WiMAX networks). The term "transmission medium" shall be taken to include any intangible medium that is capable of storing, encoding, or carrying instructions for execution by the machine, and includes digital or analog communications signals or other intangible media to facilitate communication of such software.

Figure 11:
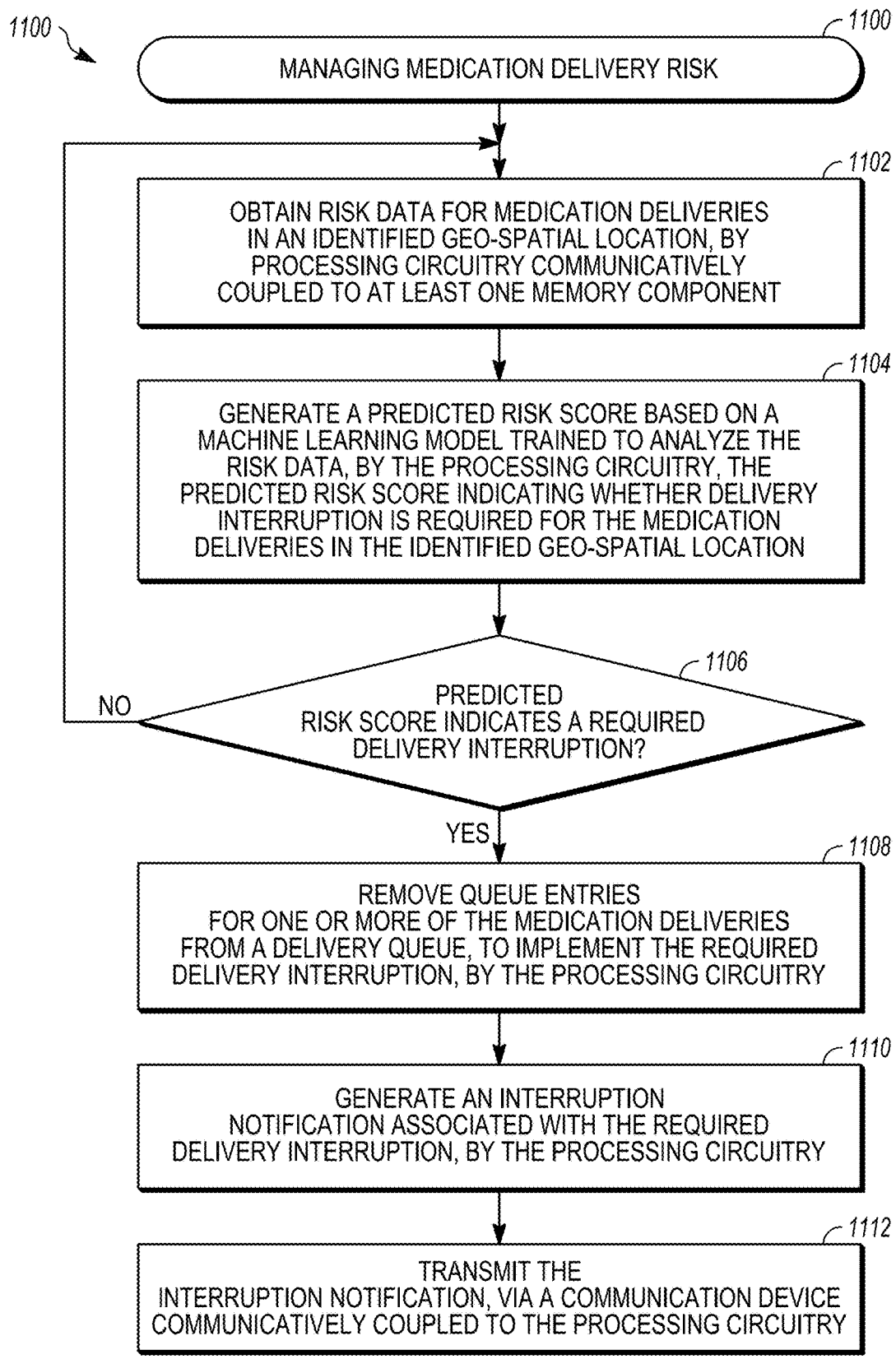
FIG. 11 is a flow chart that illustrates an embodiment of a process for managing medication delivery risk, in accordance with the disclosed embodiments.

FIG. 11 is a flow chart that illustrates an embodiment of a process 1100 for managing medication delivery risk, in accordance with the disclosed embodiments. The various tasks performed in connection with process 1100 may be performed by software, hardware, firmware, or any combination thereof. For illustrative purposes, the following description of process 1100 may refer to elements mentioned above in connection with FIGS. 1-10. In practice, portions of process 1100 may be performed by different elements of the described system. It should be appreciated that process 1100 may include any number of additional or alternative tasks, the tasks shown in FIG. 11 need not be performed in the illustrated order, and process 1100 may be incorporated into a more comprehensive procedure or process having additional functionality not described in detail herein. Moreover, one or more of the tasks shown in FIG. 11 could be omitted from an embodiment of the process 1100 as long as the intended overall functionality remains intact.

First, the process 1100 obtains risk data for medication deliveries (or non-medication deliveries) in an identified geo-spatial location, by processing circuitry communicatively coupled to at least one memory component (step 1102). One suitable methodology for obtaining risk data is described below with reference to FIG. 12. Risk data may include any data associated with environmental conditions for the geo-spatial location that may affect delivery of medications from a pharmacy fulfillment center. Typical examples of risk data may include weather event data (e.g., precipitation, temperature, snow, hurricanes, tornadoes, flooding, waves, and the like) and disaster event data (e.g., wildfires, earthquakes, civil unrest, road blockages, air traffic grounding, traffic accidents, and the like). The risk data can be any data set described herein or other germane data sets. The process 1100 identifies current and/or historical risk data associated with a particular geo-spatial location, such as a ZIP code area, a state, a county, a district, or any other defined geographic area.

Next, the process 1100 generates a predicted risk score based on a machine learning model trained to analyze the risk data, by the processing circuitry, the predicted risk score indicating whether delivery interruption is required for the medication deliveries in the identified geo-spatial location (step 1104). The process 1100 uses a machine learning model that has been previously trained using historical risk data, to analyze current risk data to determine (i) whether a standard, non-delayed medication delivery is likely to occur in the identified geo-spatial area, thus requiring no delivery interruption, or (ii) whether current risk data indicates significant delays will occur if medication delivery is attempted, and thus a delivery interruption is currently required. The process 1100 generates a predicted risk score indicating the current situation, based on output from the machine learning model.

The process 1100 then determines whether the predicted risk score indicates a required delivery interruption, based on the risk score (decision 1106). When the predicted risk score does not indicate a required delivery interruption (the "No" branch of 1106), the process 1100 returns to the beginning and continues to update by obtaining new risk data (step 1102) and generating a new predicted risk score (step 1104), which are then used to determine if a delivery interruption is indicated by the new, updated predicted risk score. In contrast, when the predicted risk score does indicate a required delivery interruption (the "Yes" branch of 1106), then the process 1100 takes active steps to implement the required delivery interruption. The predicted risk score indicates a delivery interruption when a particular medication delivery is unlikely to be successfully completed in the particular geo-spatial location within an acceptable time period, due to severe weather events, severe disaster events (whether natural or man-made), and/or any type of event that will affect delivery conditions such that significant delay is introduced into the medication delivery procedure. For example, if a particular medication will be delivered via a truck driving on a roadway in geographic area X, but there is a five-car traffic accident that has obstructed the roadway such that the truck would be unable to move forward and would therefore be delayed during delivery. In this example, the process 1100 would obtain risk data in step 1102 that includes weather data, natural disaster data, and man-made disaster data that includes the five-car traffic accident. The process 1100 would generate a predicted risk score based on a machine learning model analysis of the obtained risk data in step 1104, which would indicate that a delivery interruption is required in this situation, to prevent a temperature-sensitive or specialty medication from being located inside a truck or other delivery vehicle that may not be climate controlled in the cargo area. Thus, in this particular example, the temperature-sensitive or specialty medication would be protected from spoilage, breakdown of the physical integrity of the medication, and/or a reduction in medical efficacy or potency of the medication.

Returning to FIG. 11, the process 1100 removes queue entries for one or more of the medication deliveries from a delivery queue (step 1108). The delivery queue is used by a pharmacy fulfillment center to prioritize medication deliveries for packaging and distribution via transport (e.g., motor vehicle, manned or unmanned aircraft, trains, boats). Here, by removing queue entries for one or more of the medication deliveries, the process 1100 prevents the medications that have been identified as specialty medications requiring a short transport time, a temperature-controlled transport, or other special requirements that may not be possible to achieve if a delay is introduced, due to weather events or disaster events.

The process 1100 also generates an interruption notification associated with the required delivery interruption, by the processing circuitry (step 1110), and then transmits the interruption notification, via a communication device communicatively coupled to the processing circuitry (step 1112). In some embodiments, the interruption notification may be an alert transmitted to a personal electronic device of a customer or patient, to communicate to the customer that there is a required delivery interruption for the customer's medication such that initiation of delivery of the medication may be delayed. Due to the delay in initiating delivery of the medication, resulting in a delay of arrival of the medication at the location of the endpoint customer. Certain embodiments of the process 1100 generate the interruption notification as an electronic notification to the endpoint customer to ensure that the customer is aware of the required delivery interruption and the associated delay in medication arrival. Other embodiments of the process 1100 may generate the interruption notification as an electronic alert to the pharmacy fulfillment center personnel via a centralized computer system for the pharmacy fulfillment center and/or via personal electronic devices. Such interruption notifications provided to the pharmacy fulfillment center personnel provide information such that pharmacy personnel are aware of current and past delivery interruptions that will require future delivery.

Figure 12:
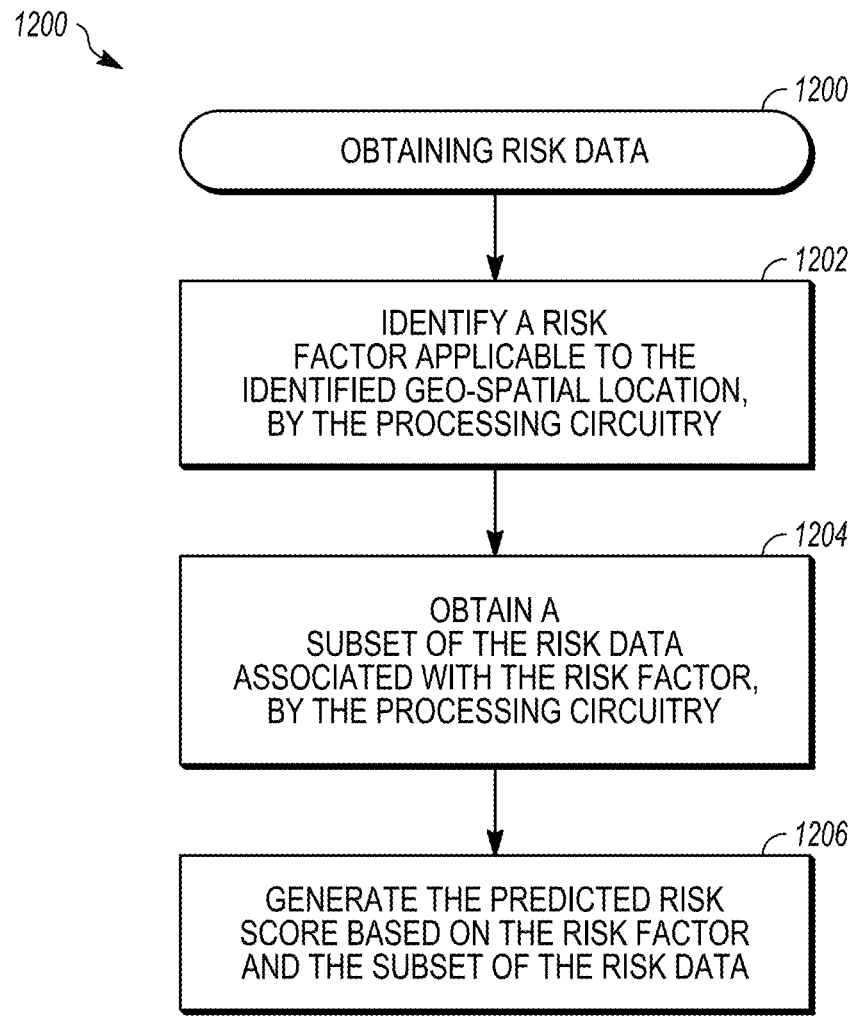
FIG. 12 is a flow chart that illustrates an embodiment of a process for obtaining risk data, in accordance with the disclosed embodiments.

FIG. 12 is a flow chart that illustrates an embodiment of a process 1200 for obtaining risk data, in accordance with the disclosed embodiments. It should be appreciated that the process 1200 described in FIG. 12 represents one embodiment of step 1102 described above in the discussion of FIG. 11, including additional detail. First, the process 1200 identifies a risk factor applicable to the identified geo-spatial location, by the processing circuitry (step 1202). As described herein, the identified geo-spatial location may include a region delineated by a set of ZIP codes (i.e., postal delivery codes), wherein the set of ZIP codes is associated with a severe weather forecast area, a disaster warning area, or other geographic area associated with one or more risk factors.

Applicability of a risk factor to a particular geo-spatial location may be indicated by the machine learning model, which has been trained using historical data for the geo-spatial area. Applicable risk factors may be associated with a particular weather event or condition; a particular disaster event or condition; or particular attributes of the geo-spatial location itself. For example, risk factors associated with a hurricane (weather event) may include high wind speeds, increased precipitation levels, and potential flooding. In a second example, risk factors associated with a rainy season of the year (weather condition) may include potential high levels of precipitation, high levels of humidity potentially affecting physical integrity of medications, and increased flooding. As another example, risk factors associated with wildfires (disaster event) may include high wind speeds and low precipitation levels creating dry conditions. In a fourth example, risk factors associated with a coastal town (attributes of the geo-spatial location) may include potential flooding.

Next, the process 1200 obtains a subset of the risk data associated with the risk factor, by the processing circuitry (step 1204). The process 1200 may obtain risk data from various data storage sources, as described previously with regard to FIG. 1. In certain embodiments, the process 1200 may obtain the subset of the risk data via at least one Application Programming Interface (API) associated with the risk factor. For example, if the identified risk factor is potential flooding in a coastal town, then the process 1200 may obtain the subset of the risk data associated with potential flooding via an API that provides current precipitation data and current beach conditions for the identified geo-spatial location. In some embodiments, the process 1200 may obtain the subset of the risk data via a web-crawler or other internet data "scraping" or data aggregation tools. Using our previous example of a risk factor of potential flooding in a coastal town, the process 1200 may use an automated software tool (e.g., a web-crawler or "bot") to obtain current precipitation conditions, current beach conditions, or the like.

The process 1200 obtains current data and historical data for the risk factor in the identified geo-spatial area. For example, if the process 1200 identifies a risk factor of potential flooding in step 1202, then the process 1200 obtains current and historical flooding data for the identified geo-spatial area. In certain embodiments, the process 1200 may identify more than one risk factor, and thus, the risk data includes relevant data for all of the risk factors. For purposes of process 1200, one risk factor is identified in step 1202 and a subset of the risk data associated with the identified risk factor is obtained in step 1204.

The process 1200 then generates the predicted risk score based on the risk factor and the subset of the risk data (step 1206). Here, the process 1200 incorporates the predictive analysis capabilities of the machine learning model. First, the machine learning model is trained using the historical data associated with the risk factor, and second, the trained machine learning model is then used to generate the predicted risk score for the current data associated with the risk factor.

Figure 13:
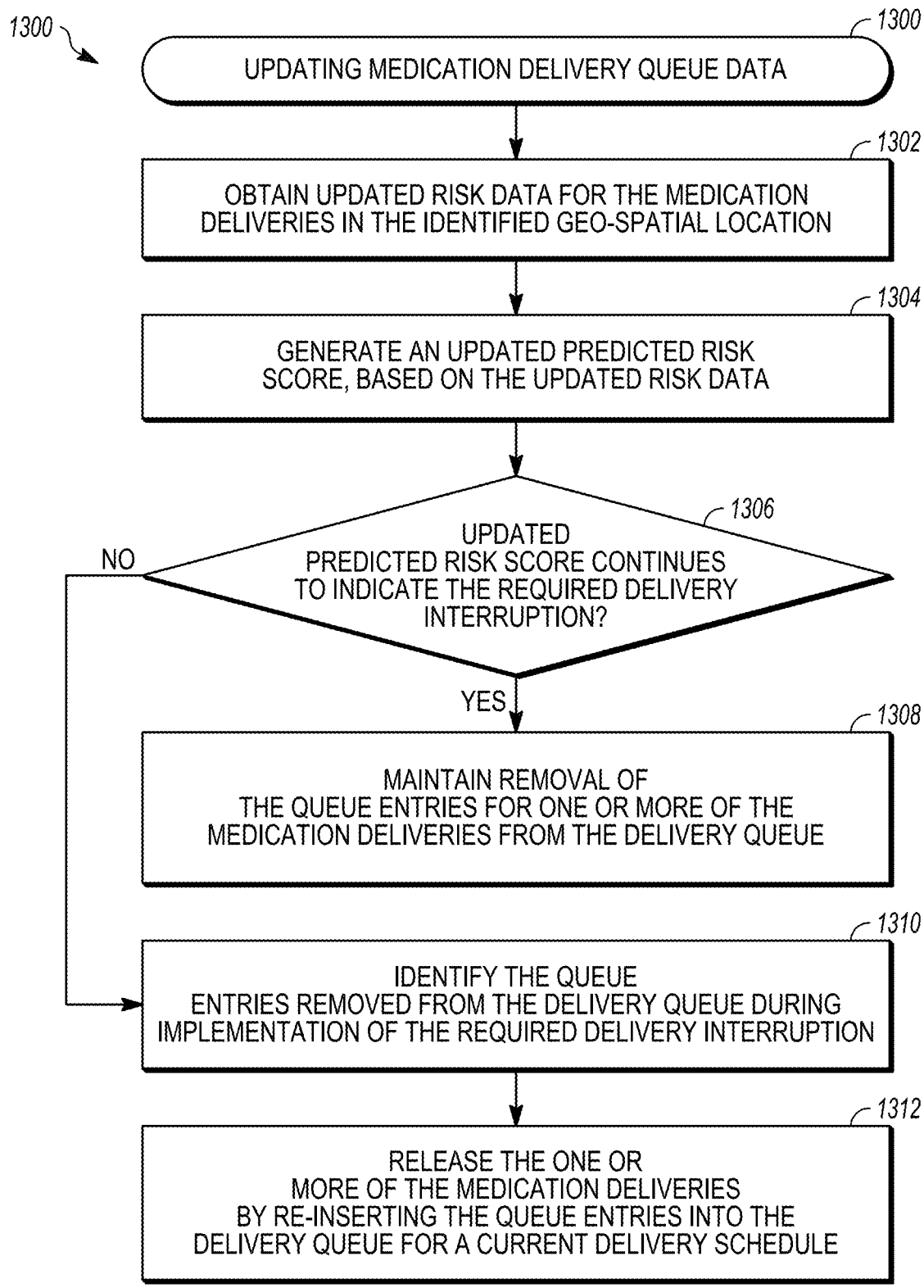
FIG. 13 is a flow chart that illustrates an embodiment of a process for updating medication delivery queue data, in accordance with the disclosed embodiments.

FIG. 13 is a flow chart that illustrates an embodiment of a process 1300 for updating medication delivery queue data, in accordance with the disclosed embodiments. As disclosed herein, the process 1300 includes steps that are performed following completion of process 1100 described above with regard to FIG. 11, for the purpose of updating the system, re-evaluating any queue entries previously removed from the queue due to a required delivery interruption, and, when appropriate, re-inserting the removed queue entries back into the queue such that the associated medication deliveries will be made according to the order of the updated queue that includes the re-inserted entries.

First, the process 1300 obtains updated risk data for the medication deliveries in the identified geo-spatial location (step 1302). In certain embodiments, updated risk data may be obtained from various data sources, as described previously with regard to FIG. 1. Typical embodiments of the process 1300 may employ an Application Programming Interface (API), web-crawler or other internet data scraping tools, data aggregation tools, and/or any type of internet-based data collection mechanism. Other embodiments of the process 1300 may obtain the updated risk data via a wired and/or wireless communication connection to a data storage device (e.g., one or more servers, hard disk drives, other types of computer-readable media) via the Internet, an intranet, or any other type of communication connection. In some embodiments, the process 1300 may employ active steps to retrieve the updated risk data. In other embodiments, the process 1300 may receive the updated risk data in the form of transmitted messages received by the process 1300.

As described previously, the updated risk data may include any data associated with severe weather events, disaster events (natural or man-made), and/or other events or circumstances that introduce an unacceptable time delay into the medication delivery process during the period of time after the medication has been packaged and shipped by the pharmacy fulfillment center. During this time, the medication may be located onboard a delivery vehicle or in a temporary storage location, and such locations may not provide appropriate temperature controls, ultraviolet light controls, and/or other medication storage controls required for particular specialty medications to maintain potency, structural integrity, or other characteristics associated with medical efficacy of the particular medication. Thus, to accommodate delivery of certain medications, delay during transit is minimized or eliminated by the process 1300 through the use of machine learning and predictive analysis to identify and use required delivery interruptions (i.e., removal of a delivery from the queue and re-insertion into the queue at a time when transit time of the medication can be minimized to an acceptable duration wherein the medication can be delivered without spoilage or otherwise being rendered unusable or ineffective).

Next, the process 1300 generates an updated predicted risk score, based on the updated risk data (step 1304). As described previously, the process 1300 generates a risk score using the machine learning model that is trained using historical risk data. Here, the process 1300 has obtained the updated risk data (in step 1302) associated with an identified geo-spatial area, such that the machine learning model may be updated and used to analyze the updated model to generate the updated predicted risk score.

When the updated predicted risk score continues to indicate the required delivery interruption (the "Yes" branch of 1306), the process 1300 maintains removal of the queue entries for one or more of the medication deliveries from the delivery queue (step 1308). However, when the updated predicted risk score does not continue to indicate the required delivery interruption (the "No" branch of 1306), the process 1300 identifies the queue entries removed from the delivery queue during implementation of the required delivery interruption (step 1310).

Such queue entries were removed from the medication delivery queue of the pharmacy fulfillment center, due to a previously determined predicted risk score indicating that delays occurring during delivery of the medication would likely cause a transit time that exceeds an allowable amount of time for the relevant medications to be in transit and likely outside of a controlled environment appropriate to store the medication. Typically, for a medication to maintain its potency, structural integrity, and/or any other characteristic required to maintain medical efficacy of the drug, the medication must be kept, stored, or otherwise located in a place where certain environmental conditions exist. For example, a particular medication may require storage between a required minimum temperature and a required maximum temperature. Specialty medications may require a narrow range of acceptable storage temperatures, while other types of medications may be appropriately stored within a wider range of acceptable storage temperatures. Room temperature range, humidity level, availability of refrigeration, and other environmental factors may be considered by the process 1300 when evaluating an appropriate transit time for a particular medication.

After determining that the updated predicted risk score does not continue to indicate the required delivery interruption (in decision 1306) and identifying the queue entries removed from the delivery queue during implementation of the required delivery interruption (in step 1310), the process 1300 then releases the one or more of the medication deliveries by re-inserting the queue entries into the delivery queue for a current delivery schedule (step 1312). Using the updated risk data and the machine learning model, the process 1300 performs predictive analysis to generate an updated predicted risk score indicating transit times compatible with maintaining integrity of the relevant medications. When conditions of the geo-spatial location were previously incompatible with the relevant medications, the queued deliveries were removed. Here, the process 1300 has determined that certain medication deliveries removed from the delivery queue (due to poor delivery conditions resulting in unacceptable transit delays) may now be added back to the queue and the medication deliveries may be completed.

Figure 14:
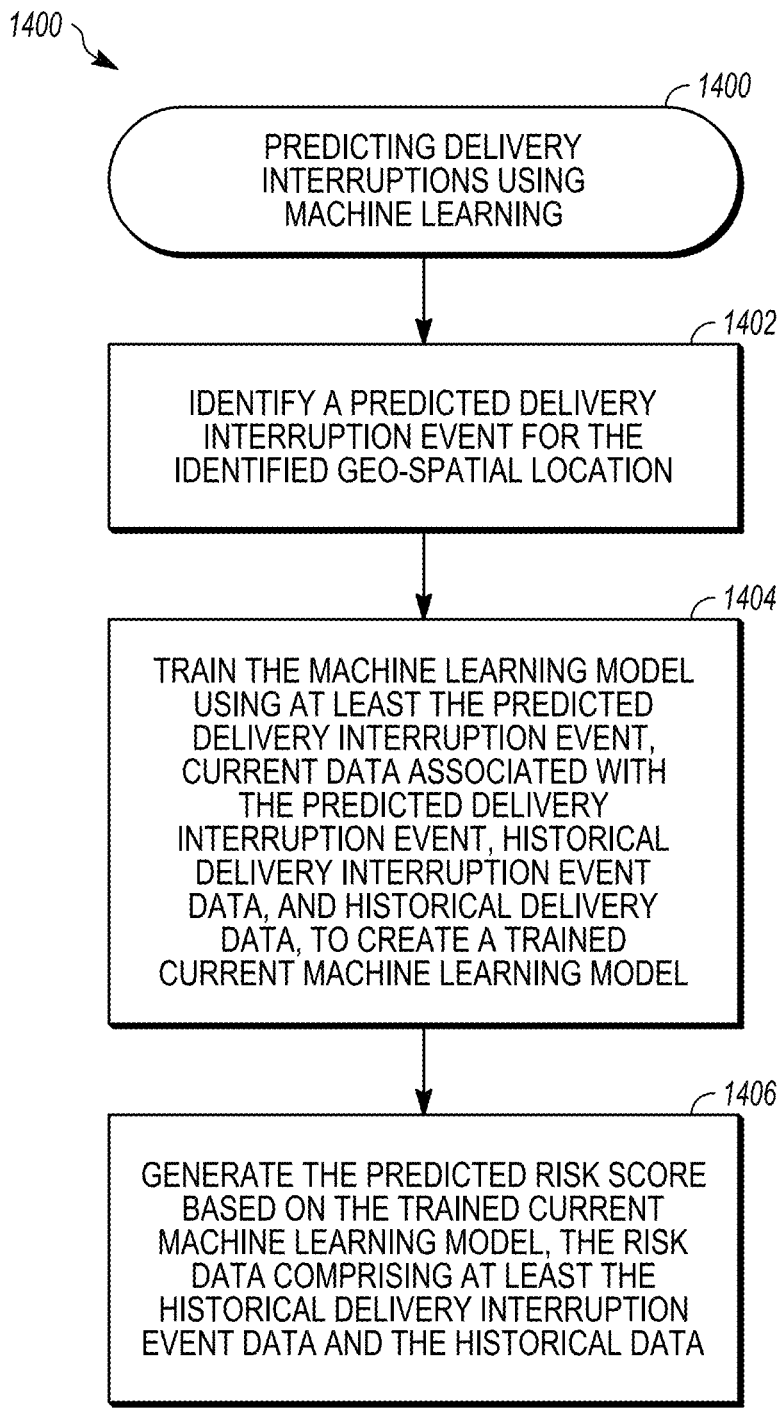
FIG. 14 is a flow chart that illustrates an embodiment of a process for predicting delivery interruptions using machine learning, in accordance with the disclosed embodiments.

FIG. 14 is a flow chart that illustrates an embodiment of a process 1400 for predicting delivery interruptions using machine learning, in accordance with the disclosed embodiments. First, the process 1400 identifies a predicted delivery interruption event for the identified geo-spatial location (step 1402). A predicted delivery interruption event is any event producing environmental conditions that may increase delivery transit times for a particular geo-spatial area, such that the transit times may exceed an allowable time duration for a medication to remain in-transit and outside of a controlled environment suitable for medication storage. A controlled environment suitable for medication storage may include controls for ambient temperature, refrigeration temperature, humidity level, and any other characteristic affecting medication potency, structural integrity, medical efficacy, or the like. During transit, medications are often located inside delivery vehicles such as a truck with a non-climate-controlled storage area, or in a temporary storage location waiting for a delivery vehicle, such as a warehouse that may or may not include environmental controls appropriate to a particular medication.

Predicted delivery interruption events may include, without limitation: severe weather events (e.g., hurricanes, tornadoes, floods), disaster events (e.g., wildfires, civil unrest, building collapse), and any other event causing extended transit times for medication deliveries from a pharmacy fulfillment center. Here, the process 1400 determines current conditions for the identified geo-spatial location via various data sources (as described previously with regard to FIG. 1) and predicts a delivery interruption event applicable to the current conditions.

Next, the process 1400 trains the machine learning model using at least the predicted delivery interruption event, current data associated with the predicted delivery interruption event, historical delivery interruption event data, and historical delivery data, to create a trained current machine learning model (step 1404). The process 1400 uses current and historical data to train the machine learning model. Current data includes the predicted delivery interruption event and the current conditions data determined in step 1402. The process 1400 obtains historical data via any relevant data source, as described previously, and/or via Application Programming Interface (API), web-crawler or other internet data scraper tool, data aggregation tools, or the like. Additional historical data may be obtained via remote server or other data storage device, Internet sources, intranet sources, connected databases, environmental conditions data aggregation services, public data resources, or the like. It should be appreciated that current data and historical data associated with the predicted delivery interruption event may be obtained via any appropriate source, based on the particular type of delivery interruption event that has been predicted.

The process 1400 then generates the predicted risk score based on the trained current machine learning model, the risk data comprising at least the historical delivery interruption event data and the historical data (step 1406). As described herein, the generated predicted risk score indicates whether a delivery interruption is required for the identified geo-spatial area under current conditions (i.e., the predicted delivery interruption event).

Some of the present examples illustrate embodiments with a focus on the location of the delivery for ease of explanation. However, disruptions to the transportation network along the predicted or known route of travel of the order may also adversely affect the delivery of the order. For example, if an order is going to be filled by a fulfillment center in the northeast and then travel on an roadway, e.g., I-90, south to a southern state, e.g., Florida, then a disruption of travel on the roadway intermediate the fulfillment center and the destination in Florida, e.g., either a distribution center or delivery location, may adversely impact delivery. The present predictive model can also take into account adverse events by generating the needed data set regarding the event and the travel of the order to predict a likely delivery delay. This will take into account delivery delays for intermediate legs in the transportation route of the order.

It is contemplated for examples described herein to extend to individual elements and concepts described herein, independently of other concepts, ideas or systems, as well as for examples to include combinations of elements recited anywhere in this application. Although examples are described in detail herein with reference to the accompanying drawings, it is to be understood that the concepts are not limited to those precise examples. As such, many modifications and variations will be apparent to practitioners skilled in this art. Accordingly, it is intended that the scope of the concepts be defined by the following claims and their equivalents. Furthermore, it is contemplated that a particular feature described either individually or as part of an example can be combined with other individually described features, or parts of other examples, even if the other features and examples make no mention of the particular feature. Thus, the absence of describing combinations should not preclude claiming rights to such combinations.

As used herein, the terms "machine-readable storage medium" or "machine readable medium," (referred to collectively as "machine-readable medium") mean the same thing and may be used interchangeably in this disclosure. The terms refer to a single or multiple storage devices and/or media (e.g., a centralized or distributed database, and/or associated caches and servers) that store executable instructions and/or data, as well as cloud-based storage systems or storage networks that include multiple storage apparatus or devices. The terms shall accordingly be taken to include, but not be limited to, solid-state memories, and optical and magnetic media, including memory internal or external to processors. Specific examples of machine-readable media include non-volatile memory, including by way of example semiconductor memory devices, e.g., erasable programmable read-only memory (EPROM), electrically erasable programmable read-only memory (EEPROM), FPGA, and flash memory devices; magnetic disks such as internal hard disks and removable disks; magneto-optical disks; and CD-ROM and DVD-ROM disks. The term machine-readable media specifically excludes carrier waves, modulated data signals, and other such media.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

As used herein, a "component" refers to a device, physical entity, or logic having boundaries defined by function or subroutine calls, branch points, APIs, or other technologies that provide for the partitioning or modularization of particular processing or control functions. Components may be combined via their interfaces with other components to carry out a machine process. A component may be a packaged functional hardware unit designed for use with other components and a part of a program that usually performs a particular function of related functions. Components may constitute either software components (e.g., code embodied on a machine-readable medium) or hardware components. A "hardware component" is a tangible unit capable of performing certain operations and may be configured or arranged in a certain physical manner. In various example embodiments, one or more computer systems (e.g., a stand-alone computer system, a client computer system, or a server computer system) or one or more hardware components of a computer system (e.g., a processor or a group of processors) may be configured by software (e.g., an application or application portion) as a hardware component that operates to perform certain operations as described herein.

A hardware component may also be implemented mechanically, electronically, or any suitable combination thereof. For example, a hardware component may include dedicated circuitry or logic that is permanently configured to perform certain operations. A hardware component may be a special-purpose processor, such as a Field-Programmable Gate Array (FPGA) or an ASIC. A hardware component may also include programmable logic or circuitry that is temporarily configured by software to perform certain operations. For example, a hardware component may include software executed by a general-purpose processor or other programmable processor. Once configured by such software, hardware components become specific machines (or specific components of a machine) uniquely tailored to perform the configured functions and are no longer general-purpose processors. It will be appreciated that the decision to implement a hardware component mechanically, in dedicated and permanently configured circuitry, or in temporarily configured circuitry (e.g., configured by software) may be driven by cost and time considerations. Accordingly, the phrase "hardware component" (or "hardware-implemented component") should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware components are temporarily configured (e.g., programmed), each of the hardware components need not be configured or instantiated at any one instance in time. For example, where a hardware component comprises a general-purpose processor configured by software to become a special-purpose processor, the general-purpose processor may be configured as respectively different special-purpose processors (e.g., comprising different hardware components) at different times. Software accordingly configures a particular processor or processors, for example, to constitute a particular hardware component at one instance of time and to constitute a different hardware component at a different instance of time.

Hardware components can provide information to, and receive information from, other hardware components. Accordingly, the herein described hardware components may be regarded as being communicatively coupled. Where multiple hardware components exist contemporaneously, communications may be achieved through signal transmission (e.g., over appropriate circuits and buses) between or among two or more of the hardware components. In embodiments in which multiple hardware components are configured or instantiated at different times, communications between such hardware components may be achieved, for example, through the storage and retrieval of information in memory structures to which the multiple hardware components have access. For example, one hardware component may perform an operation and store the output of that operation in a memory device to which it is communicatively coupled. A further hardware component may then, at a later time, access the memory device to retrieve and process the stored output.

Hardware components may also initiate communications with input or output devices and can operate on a resource (e.g., a collection of information). The various operations of example methods described herein may be performed, at least partially, by one or more processors that are temporarily configured (e.g., by software) or permanently configured to perform the relevant operations. Whether temporarily or permanently configured, such processors may constitute processor-implemented components that operate to perform one or more operations or functions described herein. As used herein, "processor implemented component" refers to a hardware component implemented using one or more processors. Similarly, the methods described herein may be at least partially processor-implemented, with a particular processor or processors being an example of hardware. For example, at least some of the operations of a method may be performed by one or more processors or processor-implemented components. Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., an API). The performance of certain of the operations may be distributed among the processors, not only residing within a single machine, but deployed across a number of machines. In some example embodiments, the processors or processor-implemented components may be located in a single geographic location (e.g., within a home environment, an office environment, or a server farm). In other example embodiments, the processors or processor-implemented components may be distributed across a number of geographic locations.

As used herein, a processor refers to any circuit or virtual circuit (a physical circuit emulated by logic executing on an actual processor) that manipulates data values according to control signals (e.g., "commands," "op codes," "machine code," etc.) and which produces corresponding output signals that are applied to operate a machine. A processor may, for example, be a CPU, a RISC processor, a CISC processor, a GPU, a DSP, an ASIC, a RFIC, or any combination thereof. A processor may further be a multi-core processor having two or more independent processors (sometimes referred to as "cores") that may execute instructions contemporaneously.

Various components are described in the present disclosure as being configured in a particular way. A component may be configured in any suitable manner. For example, a component that is or that includes a computing device may be configured with suitable software instructions that program the computing device. A component may also be configured by virtue of its hardware arrangement or in any other suitable manner.

The above description is intended to be illustrative, and not restrictive. For example, the above-described examples (or one or more aspects thereof) can be used in combination with others. Other examples can be used, such as by one of ordinary skill in the art upon reviewing the above description. The Abstract is to allow the reader to quickly ascertain the nature of the technical disclosure, for example, to comply with 37 C.F.R. § 1.72(b) in the United States of America. It is submitted with the understanding that it will not be used to interpret or limit the scope or meaning of the claims.

Also, in the above Detailed Description, various features can be grouped together to streamline the disclosure. However, the claims cannot set forth every feature disclosed herein, as examples can feature a subset of such features. Further, examples can include fewer features than those disclosed in a particular example. Thus, the following claims are hereby incorporated into the Detailed Description, with each claim standing on its own as a separate example. The scope of the examples disclosed herein is to be determined with reference to the appended claims, along with the full scope of equivalents to which such claims are entitled.

Methods and systems can generate, by the one or more processors, a push notification when a user in an identified geo-spatial location that may experience a delivery interruption. The notification can include information regarding delivery of an environmentally controlled prescription. The system can receive a reply from the user device to alter the delivery or acknowledgement that delivery will be interrupted based on a predicted event.

The system can also notify the healthcare service provider in connection with a healthcare service to be provided to a user.

The method and systems described herein can establish or update at least one or a plurality of the geospatial areas based on interrupting events, forecasted temperature, movement of an item by a carrier, satellite imagery, and calculated data navigation. The geospatial areas can be evaluated based on interrupting events.

The method and system can further use data from at least one of the user's activity tracker, smartwatch, fitness tracking software, or medication compliance tracking software to determine if user is in the geospatial area.

The systems and methods can further include adjudicating, by the one or more processors, the prescription with a service providing the mail order to establish a mail order cost for the prescription when purchased via mail order.

A computer-implemented method according to the present disclosure may include establishing, by one or more processors, a geospatial location that may be subject to a delivery interruption, generating, by the one or more processors, a push notification, when a user's package including a prescription to be filled or refilled, includes information relating to likely delay of the prescription delivery.

What is claimed is:

1. A method for managing medication delivery risk, the method comprising:
    obtaining risk data for medication deliveries and prescription fulfillment orders in an identified geo-spatial location, by processing circuitry communicatively coupled to at least one memory component;
    generating a predicted risk score based on a machine learning model trained to analyze the risk data, by the processing circuitry, the predicted risk score indicating whether delivery interruption is required for the medication deliveries in the identified geo-spatial location and whether fulfillment delay is advised for prescription fulfillment orders for the identified geo-spatial location, and the risk data including weather data and disaster data corresponding to the identified geo-spatial location;

when the predicted risk score indicates the fulfillment delay, triggering a prescription fulfillment system to delay filling the prescription fulfillment orders for the identified geo-spatial location, obtaining a dynamic time limitation period based on weather data and disaster data supplied to the machine learning model, and placing the prescription fulfillment orders in a fulfillment queue subsequent to the dynamic time limitation period; and when the predicted risk score indicates a required delivery interruption,
- determining one or more medication items of the medication deliveries identified as perishable or subject to environmental controlled delivery in an item database;
- removing queue entries for one or more of the medication deliveries which include the determined one or more medication items from a delivery queue, to implement the required delivery interruption, by the processing circuitry;
- storing medication items of the removed queue entries in an environmentally controlled state at a fulfillment center;
- generating an interruption notification associated with the required delivery interruption, by the processing circuitry;
- transmitting the interruption notification, via a communication device communicatively coupled to the processing circuitry; and
- subsequent to storing the medication items of the removed queue entries,
  - determining a transit time to deliver the stored medication items according to an output of the machine learning model,
  - determining a specified acceptable transmit duration according to at least one of a room temperature range, a humidity level, and an availability of refrigeration, and
  - in response to the transit time being less than the specified acceptable transmit duration stored in the item database for respective stored medication items, controlling one or more powered conveyors to automatically insert the medication items in one or more lines of a material transport assembly to deliver the medication items.

2. The method of claim 1, further comprising:
generating the predicted risk score using at least one of a ranking model, a propensity weighting model, or a spatial weight matrix model,
wherein the machine learning model comprises at least one of the ranking model, the propensity weighting model, or the spatial weight matrix model.

3. The method of claim 1, wherein obtaining the risk data further comprises:
identifying a risk factor applicable to the identified geo-spatial location, by the processing circuitry;
obtaining a subset of the risk data associated with the risk factor, by the processing circuitry; and
generating the predicted risk score based on the risk factor and the subset of the risk data.

4. The method of claim 3, further comprising:
obtaining the subset of the risk data, via at least one Application Programming Interface (API) associated with the risk factor.

5. The method of claim 1, further comprising:
identifying a severe weather forecast area including an overlay region, by the processing circuitry, the identified geo-spatial location including at least the overlay region; and
generating the predicted risk score based on severe weather forecast data associated with the severe weather forecast area.

6. The method of claim 5, further comprising:
identifying a set of zip codes associated with the severe weather forecast area, by the processing circuitry, the identified geo-spatial location comprising at least the set of zip codes;
determining risk factors associated with the set of zip codes;
obtaining a subset of the risk data associated with the risk factors, based on the set of zip codes; and
generating the predicted risk score based on the subset of the risk data.

7. The method of claim 1, further comprising:
identifying a regional disaster area including an overlay region, by the processing circuitry, the identified geo-spatial location including at least the overlay region; and
generating the predicted risk score based on disaster data associated with the regional disaster area.

8. The method of claim 1, further comprising:
comparing the predicted risk score to a delivery interruption threshold, by the processing circuitry; and
when the predicted risk score exceeds the delivery interruption threshold
determining the required delivery interruption is indicated.

9. A system for managing medication delivery risk, the system comprising:
at least one memory component;
a communication device configured to transmit and receive data messages over a network; and
processing circuitry communicatively coupled to the at least one memory component and the communication device, the processing circuitry configured to:
- obtain risk data for medication deliveries and prescription fulfillment orders in an identified geo-spatial location;
- generate a predicted risk score based on a machine learning model trained to analyze the risk data, the predicted risk score indicating whether delivery interruption is required for the medication deliveries in the identified geo-spatial location and whether fulfillment delay is advised for prescription fulfillment orders for the identified geo-spatial location, and the risk data including weather data and disaster data corresponding to the identified geo-spatial location;
- when the predicted risk score indicates the fulfillment delay, triggering a prescription fulfillment system to delay filling the prescription fulfillment orders for the identified geo-spatial location, obtaining a dynamic time limitation period based on weather data and disaster data supplied to the machine learning model, and placing the prescription fulfillment orders in a fulfillment queue subsequent to the dynamic time limitation period;

when the predicted risk score indicates a required delivery interruption,
- determine one or more medication items of the medication deliveries identified as perishable or subject to environmental controlled delivery in an item database;
- remove queue entries for one or more of the medication deliveries which include the determined one or more medication items from a delivery queue, to implement the required delivery interruption;
- store medication items of the removed queue entries in an environmentally controlled state at a fulfillment center;
- generate an interruption notification associated with the required delivery interruption;

transmit the interruption notification via the communication device, the data messages comprising at least the interruption notification; and subsequent to storing the medication items of the removed queue entries,
- determine a transit time to deliver the stored medication items according to an output of the machine learning model,
- determine a specified acceptable transmit duration according to at least one of a room temperature range, a humidity level, and an availability of refrigeration, and
- in response to the transit time being less than the specified acceptable transmit duration stored in the item database for respective stored medication items, control one or more powered conveyors to automatically insert the medication items in one or more lines of a material transport assembly to deliver the medication items.

10. The system of claim 9, wherein the processing circuitry is further configured to:

according to a periodic interval schedule,
- obtain updated risk data for the medication deliveries in the identified geo-spatial location;
- generate an updated predicted risk score, based on the updated risk data; and
- when the updated predicted risk score does not indicate the required delivery interruption,
  - identify the queue entries removed from the delivery queue during implementation of the required delivery interruption; and
  - release the one or more of the medication deliveries by re-inserting the queue entries into the delivery queue for a current delivery schedule.

11. The system of claim 9, wherein the processing circuitry is further configured to:

in response to a user input request,
- obtain updated risk data for the medication deliveries in the identified geo-spatial location;
- generate an updated predicted risk score, based on the updated risk data; and
- when the updated predicted risk score does not indicate the required delivery interruption,
  - identify the queue entries removed from the delivery queue during implementation of the required delivery interruption; and
  - release the one or more of the medication deliveries by re-inserting the queue entries into the delivery queue for a current delivery schedule.

12. The system of claim 9, wherein the processing circuitry is further configured to:
- identify a predicted weather event for the identified geo-spatial location;
- train the machine learning model using at least the predicted weather event, weather data associated with the predicted weather event, historical weather data, and historical delivery data, to create a trained current machine learning model; and
- generate the predicted risk score, based on the trained current machine learning model.

13. The system of claim 12, wherein the processing circuitry is further configured to:
- obtain the historical weather data for the identified geo-spatial location, the historical weather data including at least: historical weather events, previous weather conditions associated with the historical weather events, and previous weather forecasts associated with the historical weather events; and
- obtain the historical delivery data associated with the historical weather data, the historical delivery data including at least previous delivery predictions associated with the historical weather events, and previous actual delivery data associated with the historical weather events,
- wherein the risk data comprises the historical weather data and the historical delivery data.

14. The system of claim 9, wherein the processing circuitry is further configured to:
- identify a predicted disaster event for the identified geo-spatial location;
- train the machine learning model using at least the predicted disaster event, disaster data associated with the predicted disaster event, historical disaster data, and historical delivery data, to create a trained current machine learning model; and
  - generate the predicted risk score, based on the trained current machine learning model.

15. The system of claim 14, wherein the processing circuitry is further configured to:
- obtain the historical disaster data for the identified geo-spatial location, the historical disaster data including at least: historical disaster events, previous disaster conditions associated with the historical disaster events, and previous disaster forecasts associated with the historical disaster events; and
- obtain the historical delivery data associated with the historical disaster data, the historical delivery data including at least previous delivery predictions associated with the historical disaster events, and previous actual delivery data associated with the historical disaster events,
- wherein the risk data comprises the historical disaster data and the historical delivery data.

16. The system of claim 9, wherein the processing circuitry is further configured to:
- generate the predicted risk score using at least one of a ranking model, a propensity weighting model, or a spatial weight matrix model,
- wherein the machine learning model comprises at least one of the ranking model, the propensity weighting model, or the spatial weight matrix model.

17. A non-transitory, computer-readable medium containing instructions thereon, which, when executed by a processor, perform a method comprising:
- obtaining risk data for medication deliveries and prescription fulfillment orders in an identified geo-spatial location, by the processor communicatively coupled to at least the non-transitory, computer-readable medium;

generating a predicted risk score based on a machine learning model trained to analyze the risk data, by the processor, the predicted risk score indicating whether delivery interruption is required for the medication deliveries in the identified geo-spatial location and whether fulfillment delay is advised for prescription fulfillment orders for the identified geo-spatial location, the risk data including weather data and disaster data corresponding to the identified geo-spatial location, and the machine learning model comprising at least one of a ranking model, a propensity weighting model, or a spatial weight matrix model;

when the predicted risk score indicates the fulfillment delay, triggering a prescription fulfillment system to delay filling the prescription fulfillment orders for the identified geo-spatial location, obtaining a dynamic time limitation period based on weather data and disaster data supplied to the machine learning model, and placing the prescription fulfillment orders in a fulfillment queue subsequent to the dynamic time limitation period;

when the predicted risk score indicates a required delivery interruption,
 determining one or more medication items of the medication deliveries identified as perishable or subject to environmental controlled delivery in an item database;
 removing queue entries for one or more of the medication deliveries which include the determined one or more medication items from a delivery queue, to implement the required delivery interruption, by the processor;
 storing medication items of the removed queue entries in an environmentally controlled state at a fulfillment center;
 generating an interruption notification associated with the required delivery interruption, by the processor;
 transmitting the interruption notification, via a communication device communicatively coupled to the processor; and
 subsequent to storing the medication items of the removed queue entries,
  determining a transit time to deliver the stored medication items according to an output of the machine learning model,
  determining a specified acceptable transmit duration according to at least one of a room temperature range, a humidity level, and an availability of refrigeration, and
  in response to the transit time being less than the specified acceptable transmit duration stored in the item database for respective stored medication items, controlling one or more powered conveyors to automatically insert the medication items in one or more lines of a material transport assembly to deliver the medication items.

18. The non-transitory, computer-readable medium of claim 17, wherein the method further comprises:
 identifying a predicted delivery interruption event for the identified geo-spatial location;
 training the machine learning model using at least the predicted delivery interruption event, current data associated with the predicted delivery interruption event, historical delivery interruption event data, and historical delivery data, to create a trained current machine learning model; and
 generate the predicted risk score based on the trained current machine learning model, the risk data comprising at least the historical delivery interruption event data and the historical delivery data.

19. The non-transitory, computer-readable medium of claim 18, wherein the method further comprises:
 identifying a predicted weather event for the identified geo-spatial location, the predicted delivery interruption event comprising the predicted weather event, the current data comprising weather data associated with the predicted weather event;
 obtaining historical weather data for the identified geo-spatial location,
  the historical delivery interruption event data comprising the historical weather data for the identified geo-spatial location,
  the historical weather data including at least: historical weather events, previous weather conditions associated with the historical weather events, and previous weather forecasts associated with the historical weather events;
 obtaining the historical delivery data associated with the historical weather data, the historical delivery data including at least: previous delivery predictions associated with the historical weather events, and previous actual delivery data associated with the historical weather events;
 training the machine learning model using at least the predicted weather event, the weather data, the historical weather data, and the historical delivery data; and
 generating the predicted risk score for the predicted weather event, based on the trained current machine learning model.

20. The non-transitory, computer-readable medium of claim 18, wherein the method further comprises:
 identifying a predicted disaster event for the identified geo-spatial location, the predicted delivery interruption event comprising the predicted disaster event, the current data comprising disaster data associated with the predicted disaster event;
 obtaining historical disaster data for the identified geo-spatial location,
  the historical delivery interruption event data comprising the historical disaster data for the identified geo-spatial location,
  the historical disaster data including at least: historical disaster events, previous disaster conditions associated with the historical disaster events, and previous disaster forecasts associated with the historical disaster events;
 obtaining the historical delivery data associated with the historical disaster data, the historical delivery data including at least: previous delivery predictions associated with the historical disaster events, and previous actual delivery data associated with the historical disaster events;
 training the machine learning model using at least the predicted disaster event, the disaster data, the historical disaster data, and the historical delivery data; and
 generating the predicted risk score for the predicted disaster event, based on the trained current machine learning model.

* * * * *